(12) United States Patent
Zemlok et al.

(10) Patent No.: US 10,993,718 B2
(45) Date of Patent: May 4, 2021

(54) SURGICAL STAPLING APPARATUS

(71) Applicant: Covidien LP, Mansfield, MA (US)

(72) Inventors: Michael A. Zemlok, Prospect, CT (US); Adam Ross, Prospect, CT (US); Russell Pribanic, Roxbury, CT (US); Ryan Williams, New Hartford, CT (US)

(73) Assignee: COVIDIEN LP, Mansfield, MA (US)

( * ) Notice: Subject to any disclaimer, the term of this patent is extended or adjusted under 35 U.S.C. 154(b) by 160 days.

(21) Appl. No.: 16/152,935

(22) Filed: Oct. 5, 2018

(65) Prior Publication Data

US 2019/0038284 A1 Feb. 7, 2019

Related U.S. Application Data

(63) Continuation of application No. 14/025,090, filed on Sep. 12, 2013, now Pat. No. 10,111,662, which is a
(Continued)

(51) Int. Cl.
*A61B 17/072* (2006.01)
*A61B 90/90* (2016.01)
(Continued)

(52) U.S. Cl.
CPC ........ *A61B 17/07207* (2013.01); *A61B 90/90* (2016.02); *A61B 2017/00115* (2013.01);
(Continued)

(58) Field of Classification Search
CPC .. A61B 2017/00115; A61B 2017/0023; A61B 2017/00221; A61B 2017/00398;
(Continued)

(56) References Cited

U.S. PATENT DOCUMENTS 4,475,679 A * 10/1984 Fleury, Jr. ............ A61B 17/072
206/339
4,485,816 A 12/1984 Krumme
(Continued)

FOREIGN PATENT DOCUMENTS

CA 2561241 A1 3/2007
EP 1728475 A2 12/2006
(Continued)

OTHER PUBLICATIONS

European Office Action issued in corresponding European Application No. 10 251 4155 dated Sep. 11, 2019, 6 pages.
(Continued)

*Primary Examiner* — Chelsea E Stinson
*Assistant Examiner* — Mary C Hibbert-Copeland
(74) *Attorney, Agent, or Firm* — Carter, DeLuca & Farrell LLP

(57) ABSTRACT

A surgical stapling apparatus is provided and includes a housing having an actuator; an elongated member extending from the housing; an end effector disposed on an end of the elongated member, the end effector having a first jaw and a second jaw, the first jaw having a staple cartridge and the second jaw having a plurality of staple forming recesses; the staple cartridge having at least a first segment and a second segment, the first segment and the second segment each having a tissue contacting surface and staple receiving slots defined in the tissue contacting surface, the first segment and the second segment being biased toward the second jaw and movable; a biasing members for each of the first segment and the second segment; and a pressure sensor for each of the first segment and the second segment.

12 Claims, 22 Drawing Sheets

Related U.S. Application Data continuation of application No. 13/598,696, filed on Aug. 30, 2012, now Pat. No. 8,627,994, which is a continuation of application No. 13/025,262, filed on Feb. 11, 2011, now Pat. No. 8,276,801, which is a continuation-in-part of application No. 13/018,467, filed on Feb. 1, 2011, now abandoned, which is a continuation-in-part of application No. 12/796,270, filed on Jun. 8, 2010, now Pat. No. 8,360,299.

(60) Provisional application No. 61/232,826, filed on Aug. 11, 2009.

(51) Int. Cl.
*A61B 17/00* (2006.01)
*A61B 90/00* (2016.01)

(52) U.S. Cl.
CPC ........... *A61B 2017/00123* (2013.01); *A61B 2017/00221* (2013.01); *A61B 2017/00398* (2013.01); *A61B 2017/00473* (2013.01); *A61B 2017/00477* (2013.01); *A61B 2017/00845* (2013.01); *A61B 2017/00853* (2013.01); *A61B 2017/07221* (2013.01); *A61B 2017/07257* (2013.01); *A61B 2017/07271* (2013.01); *A61B 2090/065* (2016.02); *A61B 2090/0811* (2016.02)

(58) Field of Classification Search
CPC .... A61B 2017/00473; A61B 2090/065; A61B 2090/0811; A61B 17/07207
USPC .. 227/19, 175.1, 176.1, 175.2, 178.2, 180.1, 227/175.3; 606/139, 219
See application file for complete search history.

(56) References Cited

U.S. PATENT DOCUMENTS

| | | | |
|---|---|---|---|
| 5,258,007 A | 11/1993 | Spetzler et al. | |
| 5,389,098 A | 2/1995 | Tsuruta et al. | |
| 5,503,320 A | 4/1996 | Webster et al. | |
| 5,526,822 A | 6/1996 | Burbank et al. | |
| 5,630,539 A | 5/1997 | Plyley et al. | |
| 5,639,007 A | 6/1997 | Nakamura | |
| 5,685,474 A | 11/1997 | Seeber | |
| 5,833,695 A | 11/1998 | Yoon | |
| 5,876,401 A | 3/1999 | Schulze et al. | |
| 5,894,979 A | 4/1999 | Powell | |
| 6,817,508 B1 | 11/2004 | Racenet et al. | |
| 6,830,174 B2 | 12/2004 | Hillstead et al. | |
| 6,978,921 B2 | 12/2005 | Shelton, IV et al. | |
| 7,140,528 B2 | 11/2006 | Shelton, IV | |
| 7,182,239 B1 | 2/2007 | Myers | |
| 7,237,705 B2 | 7/2007 | Gaudron | |
| 7,448,525 B2 | 11/2008 | Shelton, IV et al. | |
| 7,506,790 B2 | 3/2009 | Shelton, IV | |
| 7,559,452 B2 | 7/2009 | Wales et al. | |
| 7,673,780 B2 | 3/2010 | Shelton, IV et al. | |
| 7,717,312 B2 | 5/2010 | Beetel | |
| 7,784,663 B2 | 8/2010 | Shelton, IV | |
| 8,016,855 B2 | 9/2011 | Whitman et al. | |
| 8,276,801 B2 | 10/2012 | Zemlok et al. | |
| 8,360,299 B2 | 1/2013 | Zemlok et al. | |
| 10,111,662 B2 | 10/2018 | Zemlok et al. | |
| 2003/0036755 A1 | 2/2003 | Ginn | |
| 2003/0099102 A1 | 5/2003 | Duval | |
| 2003/0130677 A1 | 7/2003 | Whitman et al. | |
| 2004/0164123 A1* | 8/2004 | Racenet ............... | A61B 17/072 227/176.1 |
| 2004/0254608 A1 | 12/2004 | Huitema et al. | |
| 2005/0070958 A1 | 3/2005 | Swayze et al. | |
| 2005/0131390 A1 | 6/2005 | Heinrich et al. | |
| 2005/0203547 A1 | 9/2005 | Weller et al. | |
| 2006/0124688 A1 | 6/2006 | Racenet et al. | |
| 2006/0212069 A1* | 9/2006 | Shelton, IV ......... | A61B 17/072 606/205 |
| 2006/0271094 A1 | 11/2006 | Hudson et al. | |
| 2006/0273135 A1 | 12/2006 | Beetel | |
| 2006/0289600 A1 | 12/2006 | Wales et al. | |
| 2006/0291981 A1 | 12/2006 | Viola et al. | |
| 2007/0179408 A1 | 8/2007 | Soltz | |
| 2007/0233161 A1 | 10/2007 | Weller et al. | |
| 2008/0283571 A1 | 11/2008 | Boyden et al. | |
| 2009/0054908 A1 | 2/2009 | Zand et al. | |
| 2009/0076534 A1 | 3/2009 | Shelton, IV et al. | |
| 2009/0090763 A1 | 4/2009 | Zemlok et al. | |
| 2009/0209990 A1 | 8/2009 | Yates et al. | |
| 2009/0234248 A1 | 9/2009 | Zand et al. | |
| 2009/0261144 A1 | 10/2009 | Sniffin et al. | |
| 2009/0302092 A1* | 12/2009 | Kasvikis ............. | A61B 17/072 227/180.1 |
| 2009/0318957 A1 | 12/2009 | Viola et al. | |
| 2010/0200637 A1 | 8/2010 | Beetel | |

FOREIGN PATENT DOCUMENTS

| | | | |
|---|---|---|---|
| EP | 1769756 | A1 | 4/2007 |
| EP | 1796754 | A2 | 6/2007 |
| EP | 1813201 | A1 | 8/2007 |
| EP | 1813206 | A1 | 8/2007 |
| EP | 1997438 | A2 | 12/2008 |
| EP | 2277458 | A1 | 1/2011 |
| JP | H05337119 | A | 12/1993 |
| JP | 2006334417 | A | 12/2006 |
| WO | 9830153 | A1 | 7/1998 |
| WO | 0230296 | A2 | 4/2002 |
| WO | 03026511 | A1 | 4/2003 |
| WO | 03049906 | A1 | 6/2003 |
| WO | 03090630 | A2 | 11/2003 |
| WO | 2010088044 | A2 | 8/2010 |

OTHER PUBLICATIONS

Canadian Office Action issued in corresponding Canadian Appln. No. 2,709,777 dated May 12, 2016.
Australian Examination Report issued in corresponding Australian Appln. No. 2013206692 dated May 19, 2016.
Japanese Office Action corresponding to Japanese Application No. 2012-017921 dated Sep. 29, 2015.
European Search Report from corresponding European Application No. EP 10 25 1306 dated of completion Dec. 2, 2010.
European Search Report for corresponding EP 10 25 1415, date of completion is Sep. 22, 2010 (3 pages).
European Search Report for corresponding EP 08 25 1988.5; completed Sep. 19, 2008; dated Oct. 17, 2008; 3 pages.
European Search Report dated Jul. 28, 2011 for EP 11 15 2266.
European Search Report for EP 12154611.3 date of completion is Aug. 1, 2012 (10 pages).
European Search Report issued in corresponding European Application No. EP 15185132 dated Jan. 20, 2016.
Japanese Office Action issued in corresponding Japanese Application No. 2015-246920 dated Mar. 27, 2017.
European Examination Report issued in European Application No. 15185132.6 dated May 26, 2017.
Canadian Office Action issued in Canadian Application No. 2,765,307 dated Nov. 9, 2017.
Japanese Notice of Allowance issued in Japanese Application No. 2015-246920 dated Aug. 3, 2017.

* cited by examiner

SURGICAL STAPLING APPARATUS

CROSS REFERENCE TO RELATED APPLICATIONS

The present application is a Continuation of U.S. patent application Ser. No. 14/025,090, filed Sep. 12, 2013, which is a Continuation of U.S. patent application Ser. No. 13/598,696, filed on Aug. 30, 2012, (now U.S. Pat. No. 8,627,994), which is a Continuation of U.S. patent application Ser. No. 13/025,262, filed on Feb. 11, 2011, (now U.S. Pat. No. 8,276,801), which is a Continuation-in-Part application claiming the benefit of and priority to U.S. patent application Ser. No. 13/018,467, filed on Feb. 1, 2011, (now abandoned), which is a Continuation-in-Part application claiming the benefit of and priority to U.S. patent application Ser. No. 12/796,270, filed on Jun. 8, 2010, (now U.S. Pat. No. 8,360,299), which claims the benefit of and priority to U.S. Provisional Patent Application Ser. No. 61/232,826, filed on Aug. 11, 2009, the entire contents of each of which are incorporated herein by reference.

BACKGROUND

1. Technical Field

The present disclosure relates to surgical stapling apparatuses that are capable of applying lines of fasteners to tissue while cutting the tissue between those fastener lines and, more particularly, to improvements relating to fastener deployment and formation.

2. Background of Related Art

Endoscopic and laparoscopic surgical apparatuses are often preferred over traditional open surgical devices since a smaller incision tends to reduce the post-operative recovery time and complications. The use of laparoscopic and endoscopic surgical procedures has been relatively popular and has provided additional incentive to develop the procedures further. In laparoscopic procedures, surgery is performed in the interior of the abdomen through a small incision. Similarly, in endoscopic procedures, surgery is performed in any hollow viscus of the body through narrow endoscopic tubes inserted through small entrance wounds in the skin.

Laparoscopic and endoscopic procedures generally require that the surgical region be insufflated. Accordingly, any instrumentation inserted into the body must be sealed to ensure that gases do not enter or exit the body through the incision. Moreover, laparoscopic and endoscopic procedures often require the surgeon to access organs, tissues and/or vessels far removed from the incision. Thus, apparatuses used in such procedures are typically long and narrow while being functionally controllable from a proximal end of the apparatus.

Significant development has gone into a range of endoscopic surgical apparatuses that are suitable for precise placement of a distal end effector at a desired surgical site through a cannula of a trocar. These distal end effectors engage the tissue in a number of ways to achieve a diagnostic or therapeutic effect (e.g., endocutter, grasper, cutter, staplers, clip applier, access device, drug/gene therapy delivery device, and energy device using ultrasound, RF, laser, etc.).

Known surgical stapling apparatuses include an end effector that makes a longitudinal incision in tissue and subsequently applies lines of fasteners on opposing sides of the incision. The end effector includes a pair of cooperating jaws that, if the apparatus is intended for endoscopic or laparoscopic applications, are capable of passing through a cannula passageway. One of the jaws receives a fastener cartridge having at least two laterally spaced rows of fasteners. The other jaw defines an anvil having fastener-forming pockets aligned with the rows of fasteners in the cartridge. The apparatus includes a plurality of reciprocating wedges or cam bars which, when driven distally, pass through openings in the fastener cartridge and engage drivers supporting the fasteners to effect the firing of the fasteners toward the anvil.

Small videoscopes of various types (e.g., endoscopes) may be relied upon to monitor proper positioning and operation of the surgical stapling apparatus. While effective to a degree, it is desirable to have improved monitoring of operation of the surgical stapling apparatus. When utilizing stapling devices containing multiple fasteners in each cartridge load, it is also beneficial to determine which fasteners are being deployed and whether they are being formed properly.

Consequently, a continuing need exists for an improved surgical stapling and severing apparatus that incorporates fastener deployment and formation pressure monitoring capabilities to assure the mechanical and hemostatic integrity of a surgical stapling device.

SUMMARY

In accordance with the present disclosure, a surgical stapling apparatus is disclosed. The surgical stapling apparatus has a housing having an actuator; an elongated member extending from the housing; an end effector disposed on one end of the elongated member, the end effector including first and second jaws; a plurality of fasteners disposed in the end effector; a plurality of pusher members located in the end effector, each pusher member in the plurality of pusher members operatively coupled to a number of fasteners; an actuation mechanism operatively coupled to the actuator, the actuation mechanism including a longitudinally translatable drive member and an actuation sled coupled thereto, the actuation sled configured for engaging the plurality of pusher members; and a pressure responsive element disposed in one of the jaws, the pressure responsive element communicating a signal to a controller coupled to the surgical stapling apparatus, the signal representative of pressure applied to the pressure responsive element.

In one embodiment, interaction between the actuation sled and the pusher members applies pressure to the pressure responsive element. The pressure responsive element includes staggered pressure sensors in a circuit. The circuit, in some manifestations is a printed pressure circuit or a flexible circuit disposed on the surface of a channel positioned in one of the jaws.

In another embodiment, the surgical stapling apparatus can include a circuit that is disposed on the external surface of at least one of the jaws. In this version, the stapling apparatus also includes a beam, the beam disposed on the external surface of at least one of the jaws and seated in a groove disposed within at least one of the jaws so that the beam can be configured to translate along the groove. The beam may be an I-beam or an E-beam.

The circuit can have a laminate layer on the circuit and may even have a lubricant coating on the laminate layer. The signal communicated to the controller will from time to time be read by the controller as irregular. In such a case, the controller will activate a feedback response such as an error code, warning, or it may even stop fastener deployment altogether. It is contemplated that the pressure responsive element communicates the signal to the controller through by any of the following: voltage, resistance, impedance, electromagnetism, radio frequency, current, inductance, capacitance, infrared, optics, or any combination thereof.

Another embodiment envisions a knife configured to translate through the jaw to cut tissue. However, upon certain predetermined irregularities, the controller can prevent the knife from cutting, should those irregularities fall within those predetermined conditions. An encoder is configured to recognize irregular component positions relative to the pressure applied and send a signal to the controller. The encoder may be configured to recognize irregular positions of various components including the actuation mechanism, the knife, the actuator, the actuation sled, the pusher member, the first jaw, the second jaw, or even various combinations thereof. These encoders can be linear or rotational.

Certain embodiments contemplate the circuit including a cartridge identifying feature. Other embodiments can have controller configured to set positional limitations and run mode for a particular load or fastener type. Still further, one of the jaws may be configured and dimensioned to house a non-linear cartridge.

In other embodiments, the controller includes an end user feedback communication feature. The end user feedback communication feature is configured to communicate the feedback to an end user through percipient signals such as audible, visual, tactile, or any combination thereof.

According to another aspect of the present disclosure, a surgical stapling apparatus is provided and includes a housing having an actuator; an elongated member extending from the housing; an end effector disposed on an end of the elongated member, the end effector having a first jaw and a second jaw, the first jaw having a staple cartridge and the second jaw having a plurality of staple forming recesses; the staple cartridge having at least a first segment and a second segment, the first segment and the second segment each having a tissue contacting surface and staple receiving slots defined in the tissue contacting surface, the first segment and the second segment being biased toward the second jaw and movable; a biasing members for each of the first segment and the second segment; and a pressure sensor for each of the first segment and the second segment.

The surgical stapling apparatus may further include a component for determining when the pressure is above a threshold value.

The surgical stapling apparatus may further include a motor operatively connected to the actuator. The motor may be in the housing.

The surgical stapling apparatus may further include a power source in the housing and operatively connected to the motor.

The component may be programmed to stop the motor.

The staple forming recesses and the staple receiving slots may define linear rows. The linear rows may extend transversely with respect to a longitudinal axis of the elongated member. The staple forming recesses and the staple receiving slots may define an angle with respect to a longitudinal axis of the end effector.

According to a further aspect of the present disclosure, an end effector for selective connection to a surgical apparatus, is provided and includes a first jaw; a staple cartridge supported on the first jaw, the staple cartridge defining a tissue contacting surface, wherein the staple cartridge is divided into a plurality of independent, separately movable segments, and at least one staple retaining slot is defined in each segment; a second jaw connected to the first jaw, the second jaw supporting an anvil, the anvil defining a plurality of staple forming recesses arranged in juxtaposed correspondence with the plurality of staple retaining slots of the staple cartridge; and a pressure sensing element interposed between each staple cartridge segment and the first jaw, wherein each pressure sensing element senses a force exerted on each respective staple cartridge segment.

The end effector may further include a biasing member interposed between each staple cartridge segment and the first jaw. The biasing members may maintain each staple cartridge segment spaced a distance from the first jaw.

The staple cartridge may define at least two parallel rows of staple retaining slots. At least one substantially adjacent staple retaining slot from each row of staple retaining slots may be provided in each staple cartridge segment.

The biasing members may compress upon exertion of a force on the tissue contacting surface of any of the staple cartridge segments.

According to still another aspect of the present disclosure, an electro-surgical stapling system is provided and includes a powered surgical apparatus and an end effector. The powered surgical apparatus includes a handle portion configured and adapted to releasably connect a surgical stapling end effector thereto, the handle portion including an actuator for connection to the end effector and for driving the end effector, a motor for driving the actuator, a power source for powering the motor, and a controller for controlling at least one of the power source and the motor. The end effector is configured for selective connection to the handle portion of the powered surgical apparatus. The end effector includes a first jaw; a staple cartridge supported on the first jaw, the staple cartridge defining a tissue contacting surface, wherein the staple cartridge is divided into a plurality of independent, separately movable segments, and at least one staple retaining slot is defined in each segment; a second jaw connected to the first jaw, the second jaw supporting an anvil, the anvil defining a plurality of staple forming recesses arranged in juxtaposed correspondence with the plurality of staple retaining slots of the staple cartridge; and a pressure sensing element interposed between each staple cartridge segment and the first jaw, wherein each pressure sensing element senses a force exerted on each respective staple cartridge segment. Each pressure sensing element is in electrical communication with the controller. The controller stops at least one of approximation of the first jaw and the second jaw, and firing of the powered surgical apparatus when a force exerted on at least one of the staple cartridge segments and sensed by the respective pressure sensing elements exceeds a predetermined threshold force.

The end effector may further include a biasing member interposed between each staple cartridge segment and the first jaw. The biasing members may maintain each staple cartridge segment spaced a distance from the first jaw.

The staple cartridge of the end effector may define at least two parallel rows of staple retaining slots. At least one substantially adjacent staple retaining slot from each row of staple retaining slots may be provided in each staple cartridge segment.

The biasing members of the end effector may compress upon exertion of a force on the tissue contacting surface of any of the staple cartridge segments.

The first jaw and the second jaw of the end effector may be configured for parallel approximation.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION OF EMBODIMENTS

Figure 1A:
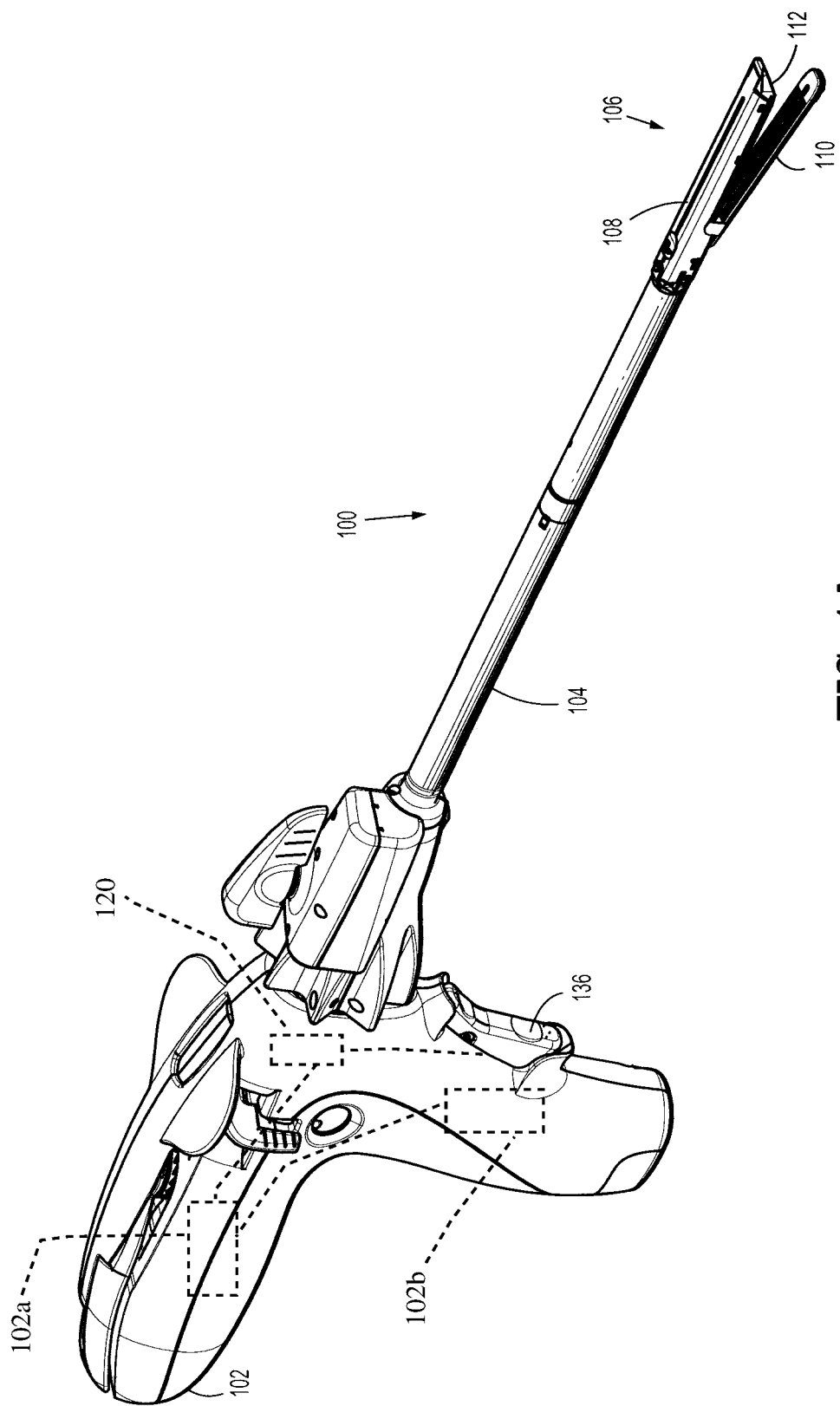
FIG. 1A is a perspective view of a powered surgical stapling apparatus.

Embodiments of the presently disclosed surgical stapling apparatus will now be described in detail with reference to the drawings, in which like reference numerals designate identical or corresponding elements in each of the several views.

As shown in the drawings and as described throughout the following description, and as is traditional when referring to relative positioning on an object, the term "proximal" refers to the end of the apparatus that is closer to the user and the term "distal" refers to the end of the apparatus that is further from the user. In the following description, well-known functions or constructions are not described in detail to avoid obscuring the present disclosure in unnecessary detail.

Figure 1B:
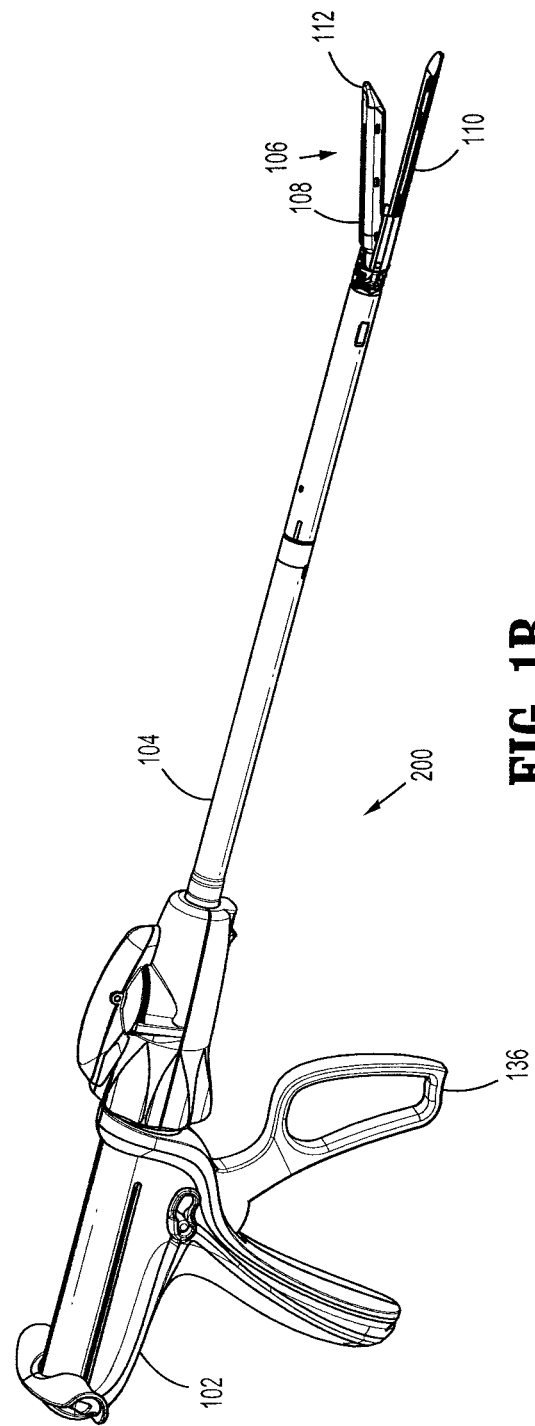
FIG. 1B is a perspective view of a manual surgical stapling apparatus.

FIG. 1A illustrates a powered surgical stapling apparatus shown generally as 100. FIG. 1B illustrates a manual surgical stapling apparatus shown generally as 200. Briefly, the surgical stapling apparatus 100, 200 includes a housing 102 having an actuator 136, an elongated member 104 extending from the housing 102, and an end effector 106 disposed on one end of the elongated member 104. As shown in FIG. 1, the housing 102 supports a motor 102a, a power source 102b (e.g., a battery), and a controller 120 therein that are operatively coupled together and to the actuator 136 for firing fasteners supported in the end effector 106 as described in greater detail hereinbelow. From FIGS. 1C-1D, the end effector 106 includes first and second jaws 108, 110, a plurality of fasteners 114 (e.g., staples) disposed in the end effector 106 and a plurality of pusher members 130 located in the end effector 106. Each pusher member 130 in the plurality of pusher members 130 is operatively coupled to a number of fasteners 114. As seen in FIGS. 3A-4B, the surgical stapling apparatus 100, 200 includes an actuation mechanism 138 operatively coupled to the actuator 136. The actuation mechanism 138 includes a longitudinally translatable drive member 140 and an actuation sled 132 coupled thereto. The actuation sled 132 is configured for engaging the plurality of pusher members 130.

Figure 1C:
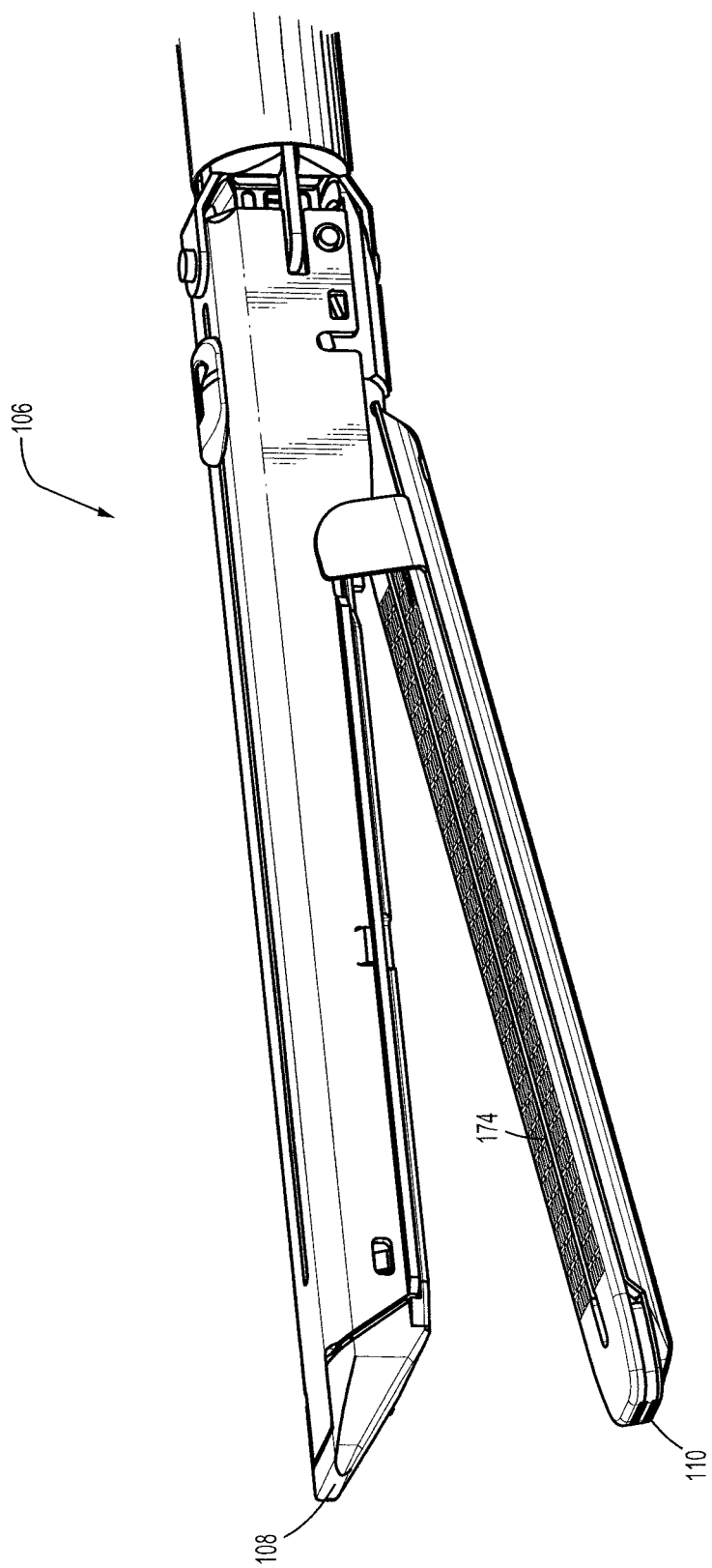
FIG. 1C is an enlarged perspective view of the end effector of a surgical stapling apparatus.
Figure 2:
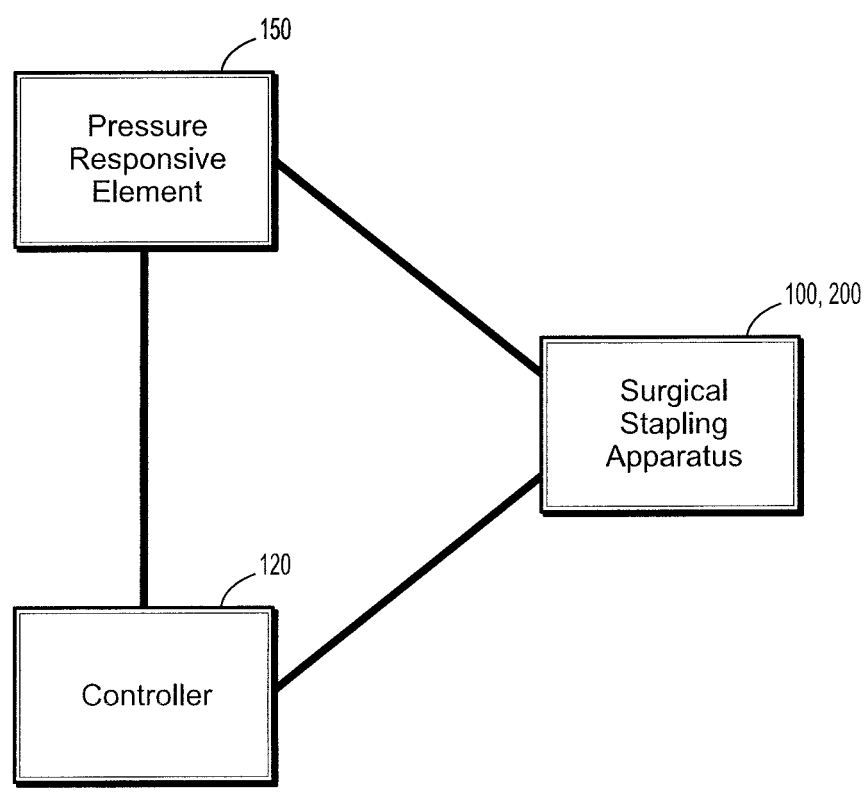
FIG. 2 is a schematic view of a surgical stapling system in accordance with the present disclosure.

In accordance with one embodiment of the present disclosure, FIG. 2 diagrams a surgical stapling system having a surgical stapling apparatus 100, 200, the surgical stapling apparatus 100, 200 having a pressure responsive element 150 and the controller 120. It is envisioned that the pressure responsive element is disposed in one of the jaws 108, 110 (FIGS. 3A-3B and 8A-8B). The pressure responsive element 150 can communicate a pressure signal 152 (not shown) to the controller 120 coupled to the surgical stapling apparatus 100, 200. The controller 120 is a microcontroller or an analog circuit which enables control, positioning, status, and fastener 114 quality feedback. The pressure signal 152 is representative of pressure applied to the pressure responsive element 150. It is envisioned that this embodiment may include a knife 164 or be knifeless, the knife 164 slidably translatable through a knife slot 174 (FIG. 1C).

Figure 5:
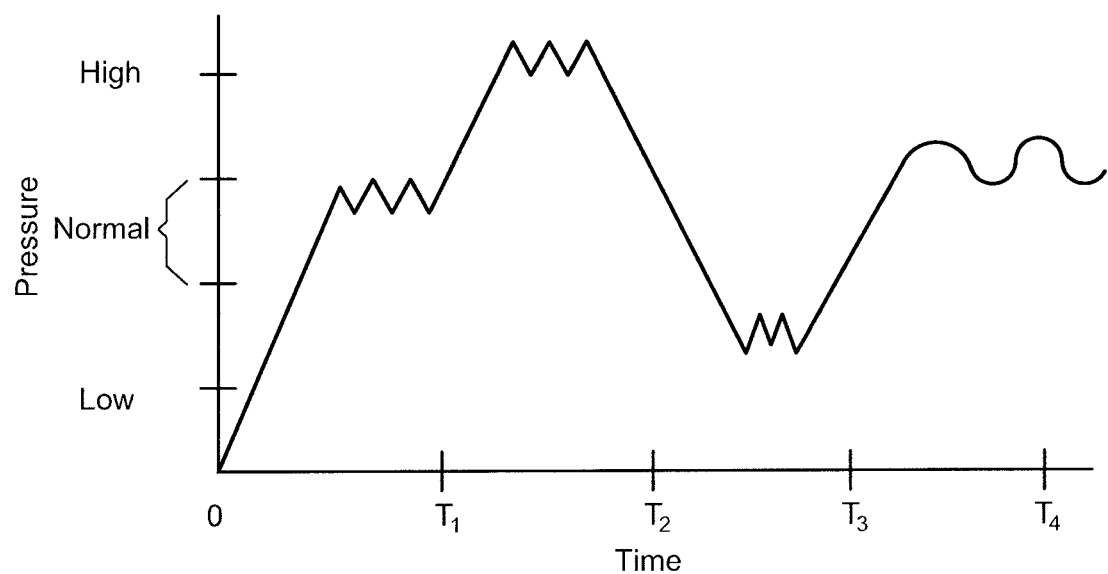
FIG. 5 is a plot of the pressure applied to form staples versus time.

Referring to FIG. 5, applied pressure may be measured in the form of waveform pulsations as seen in the time versus applied pressure graph. For example, a normal sample might read in accordance with the graph covering the time period from 0-t1. If the waveform pulsations indicate a low (t2-t3) or high (t1-t2) pressure during a certain sampling, this could be an indication that the fasteners 114 are not being properly deployed or formed due to improper applied pressure distribution necessary for proper fastener 114 deployment or formation. Alternatively, if the waveform is not a shape that has been correlated with successful test waveforms (t3-t4), an error code or feedback is initiated by the controller 120 to stop deployment or formation progression. This gives the end user the ability to properly understand the performance irregularity before proceeding or backing out.

Figure 3A:
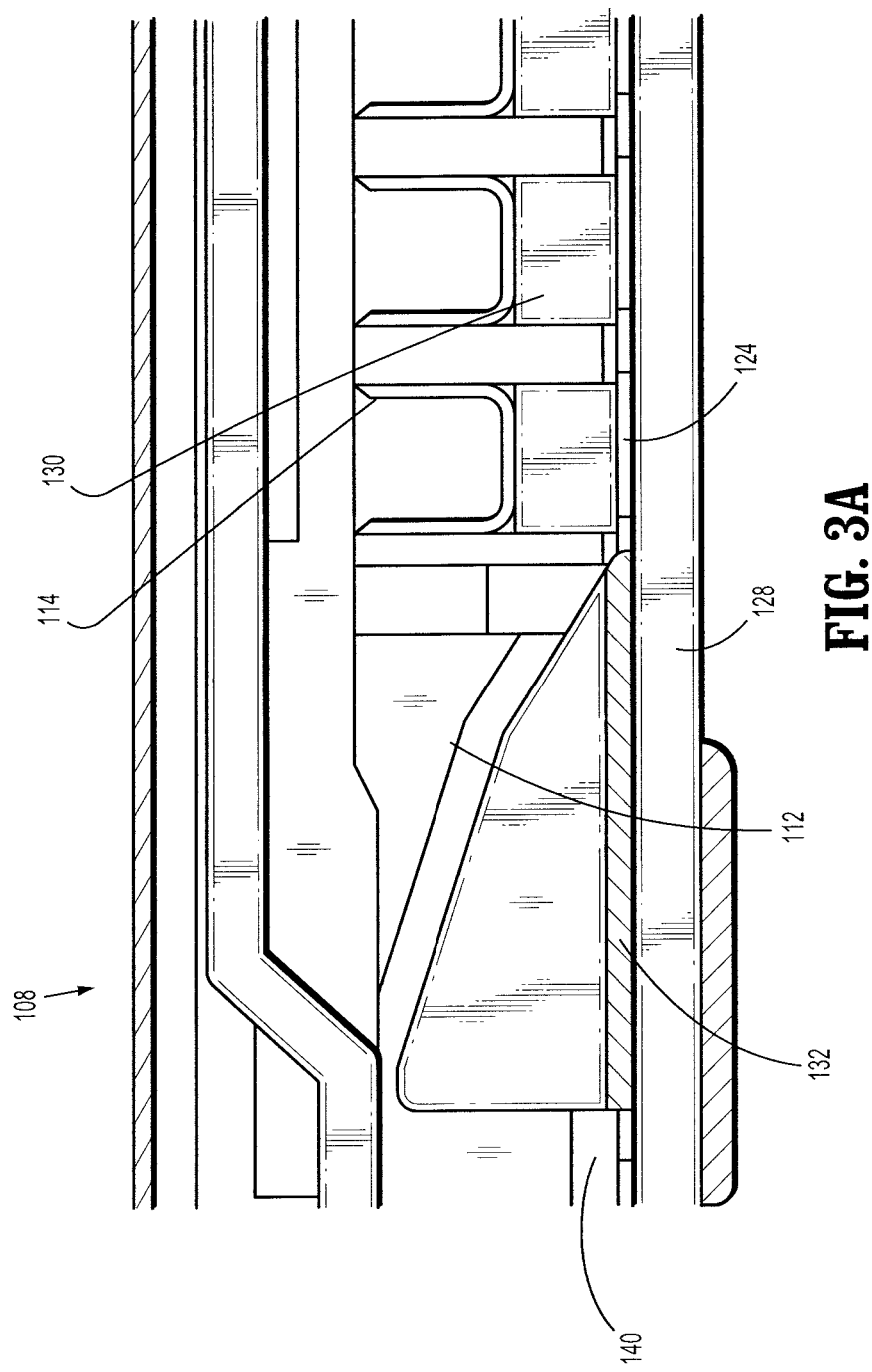
FIG. 3A is a side cross-sectional view of a portion of the end effector of the surgical stapling apparatus' of FIGS. 1A and 1B.
Figure 3B:
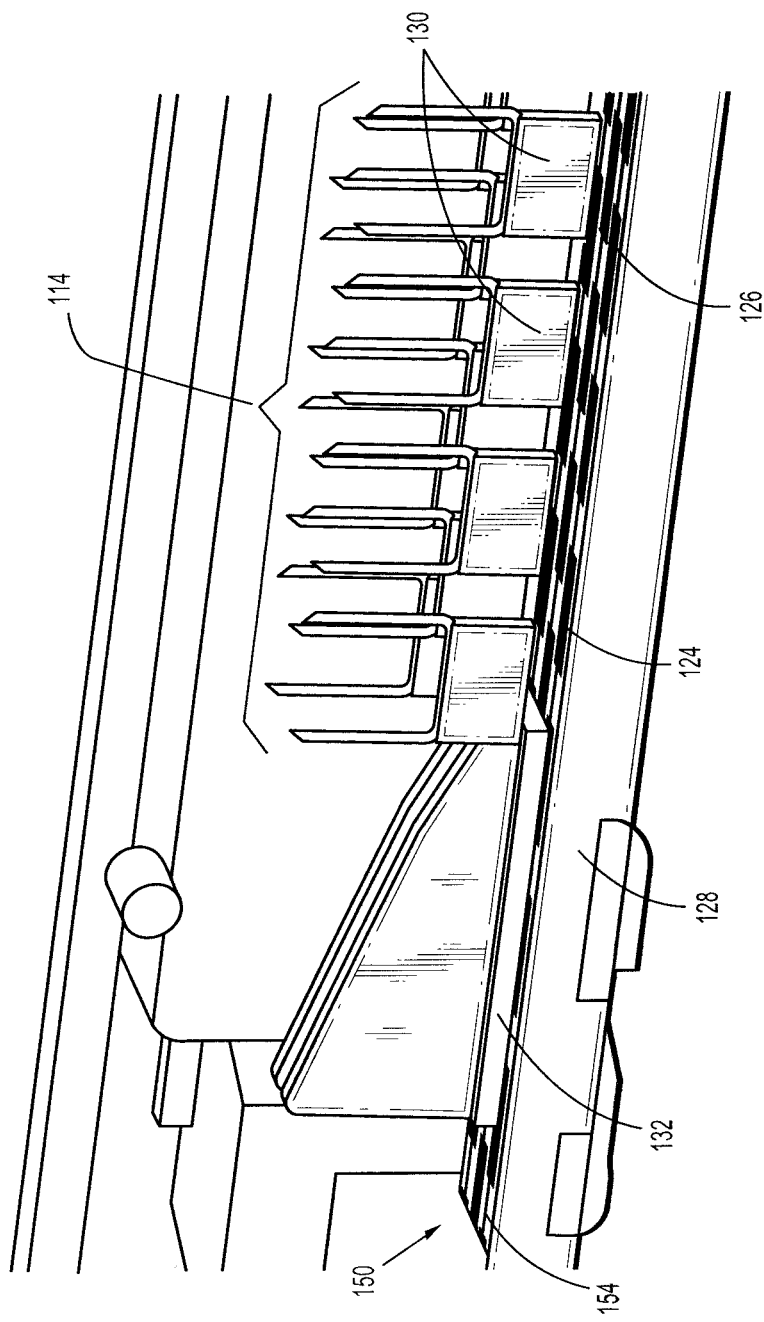
FIG. 3B is a side cross-sectional view of a portion of the end effector of the surgical stapling apparatus' of FIGS. 1A and 1B with a cartridge wall removed for clarity.

As seen in FIGS. 3A-3B, the first jaw 108 includes a cartridge channel 128 for receiving a cartridge 112. The cartridge 112 includes a plurality of fasteners 114 disposed therein. Typically, fasteners 114 are in the form of a plurality of surgical staples. The cartridge 112 houses the fasteners 114 in a plurality of linear rows, which are operatively coupled to the pusher members 130.

Figure 6:
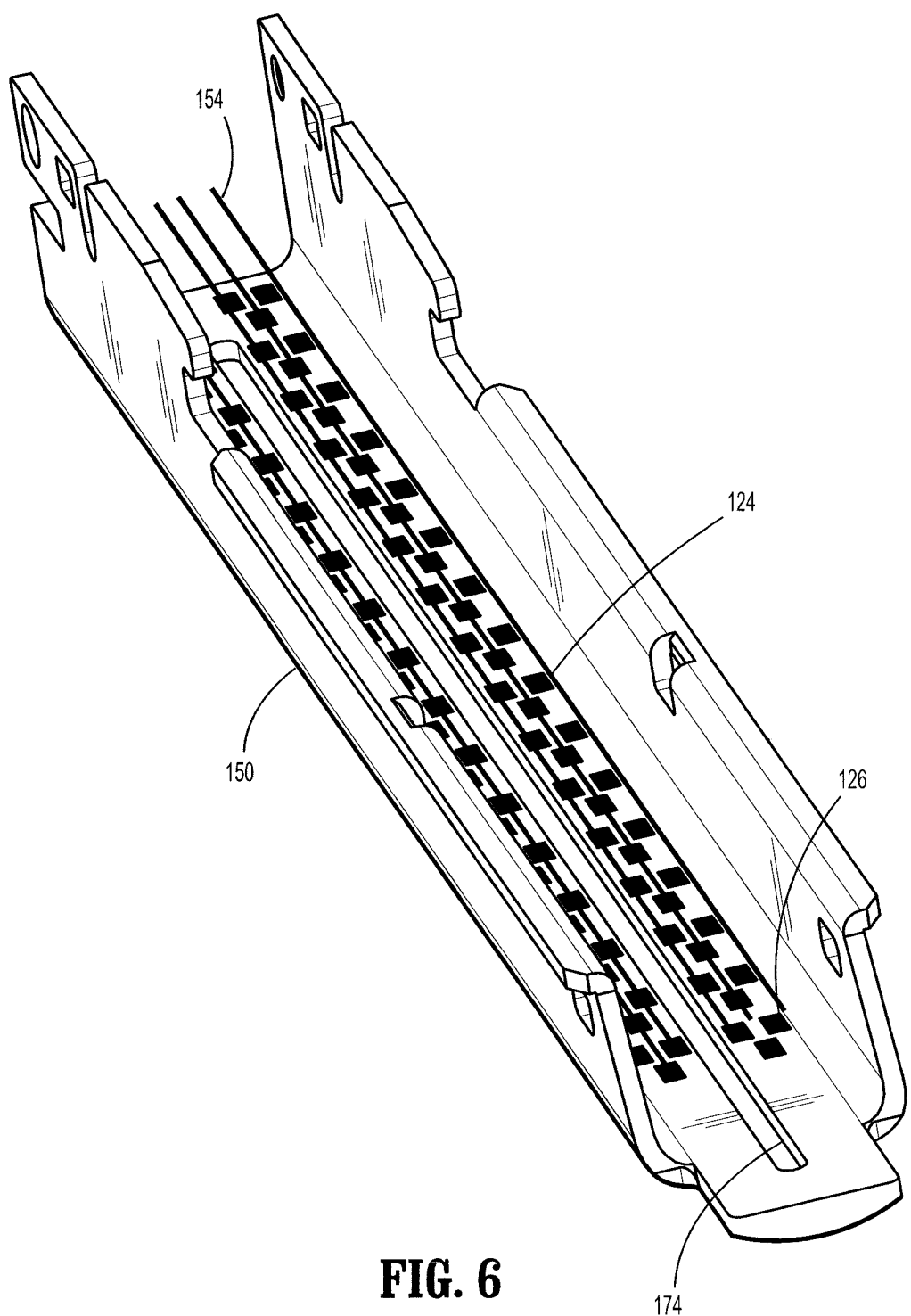
FIG. 6 is a perspective view of the interior channel of the cartridge with a printed pressure circuit disposed therein.

Referring now to FIG. 6, the pressure responsive element 150 of one manifestation includes a circuit 124 wherein at least one lead 154 connects at least one pressure sensor 126. It is also contemplated that a plurality of pressure sensors 126 are disposed on the surgical stapling apparatus 100, 200. In one instance, a lead 154 extends across a plurality of pressure sensors 126 in linear progression along the longitudinal axis, wherein at least one pressure sensor 126 corresponds to each fastener 114 or pusher member 130. Each linear row of fasteners 114 and/or pusher members 130 is connected by at least one lead 154 extending along the linear row and along the longitudinal axis of the circuit 124. The circuit 124 is a flexible or a printed pressure circuit 124.

In this embodiment, the circuit 124 is adhered to the top (working) surface of the cartridge channel 128 so that the circuit 124 can interact with the actuation sled 132 that translates therethrough. In other words, the circuit 124 is disposed within the cartridge channel 128 to matingly engage the actuation sled 132 as the actuation sled 132 translates through the cartridge channel 128 (FIGS. 3A-3B).

Figure 7:
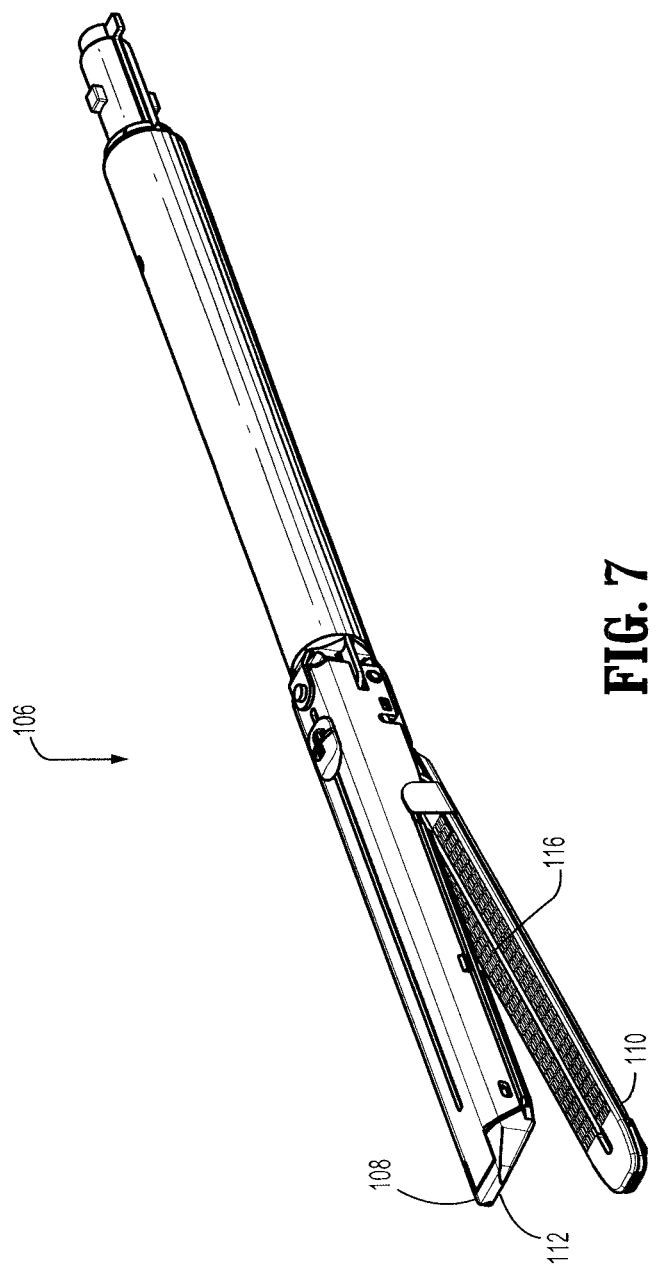
FIG. 7 is a perspective view of a removable end effector of FIGS. 1A and 1B illustrating a knife slot in one of the jaws.
Figure 8A:
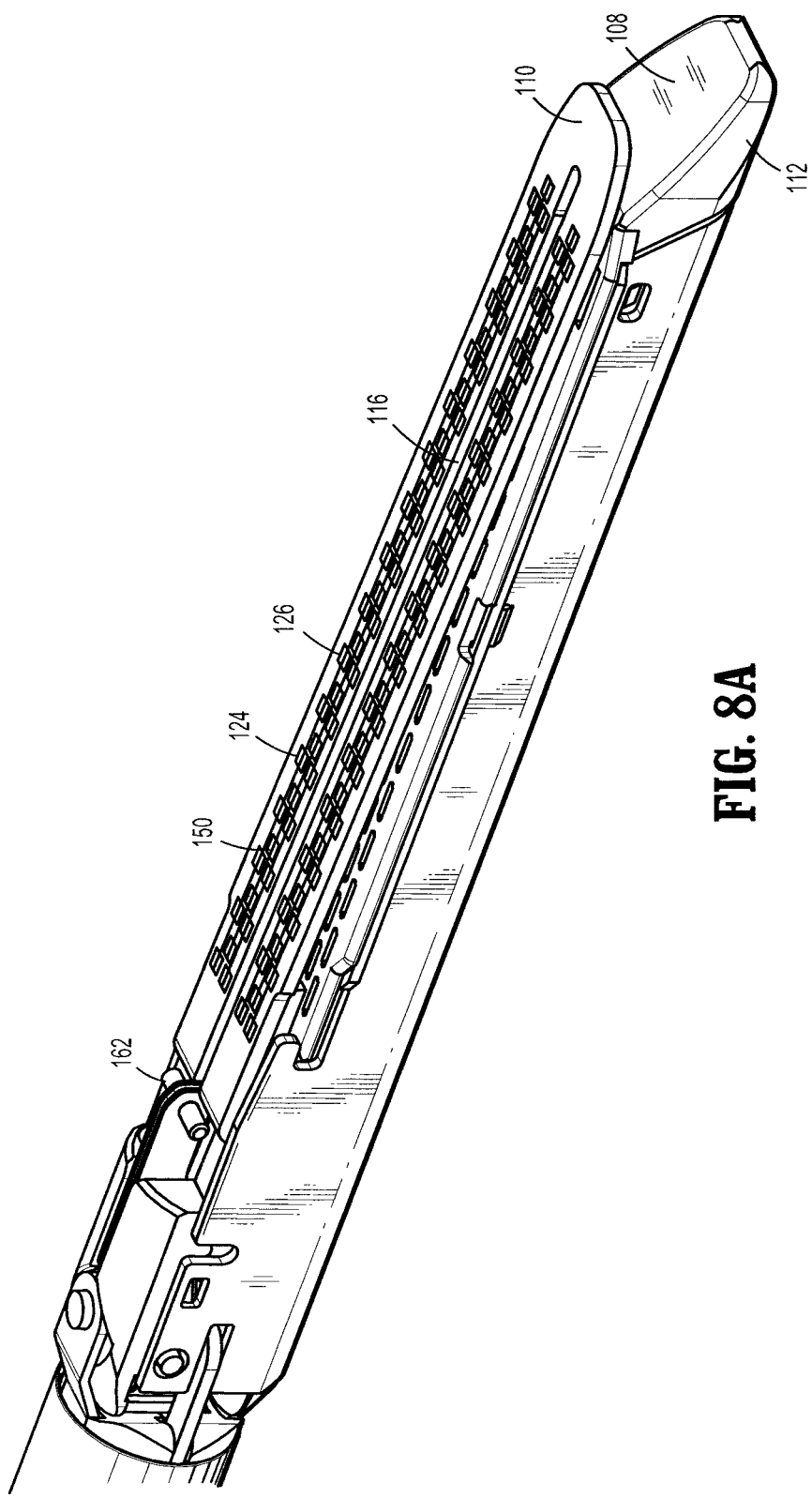
FIG. 8A is a perspective view of the end effector of FIG. 7 with the anvil cover removed for clarity showing a pressure circuit.
Figure 8B:
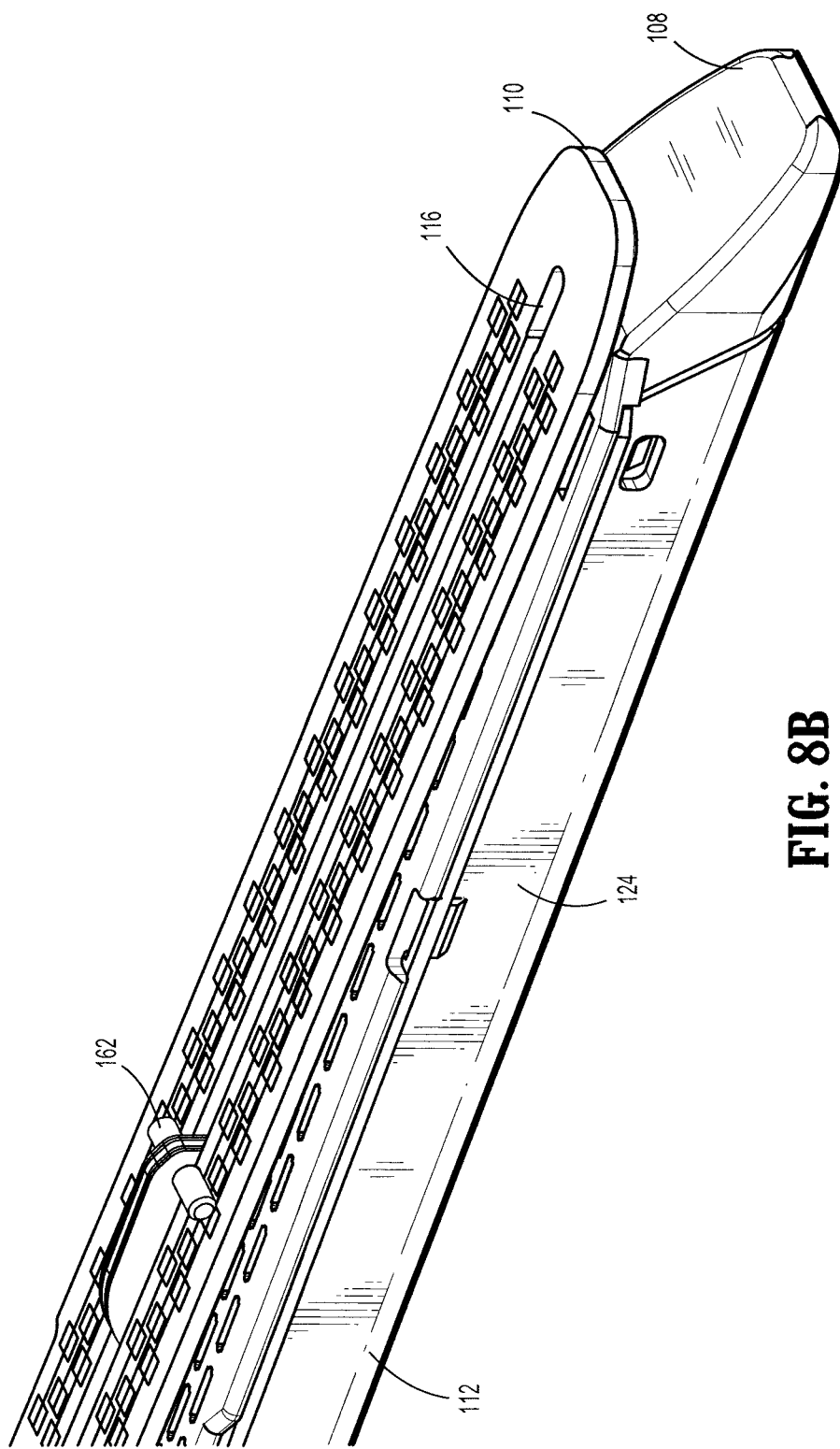
FIG. 8B is an enlarged perspective view of the embodiment disclosed in FIG. 8A.

FIGS. 7-8B show another embodiment of the surgical stapling apparatus 100, 200. As seen in FIGS. 8A-8B, the surgical stapling apparatus 100, 200 includes a pressure responsive element 150 that includes a circuit 124 and is disposed on the external surface of at least one of the jaws 108, 110. Preferably, the circuit 124 is disposed on the external surface of the second jaw 110. This embodiment includes a beam 162. The beam 162 is disposed on the external surface of at least one of the jaws 108, 110. Preferably, the beam 162 is disposed on the external surface of the second jaw 110. It is also contemplated that the beam 162 is slidably seated in a groove 116 disposed within at least one of the jaws 108, 110 and connected to the actuation sled 132 (FIGS. 8A and 8B). The beam 162 is slidably seated in a groove 116 disposed within the second jaw 110. The beam 162 is configured to translate along the groove 116. The beam is an I-beam or an E-beam. This circuit 112 is envisioned to be very thin with respect to the surgical stapling apparatus 100, 200, having dimensions at least geometrically thin enough as to not compromise or greatly impact the overall cartridge 112 size or function.

In some manifestations, the pressure sensors 126 are staggered (FIGS. 3B, 6, 8A, 8B). The circuit 124 in one arrangement is staggered and optimized so that detailed information can be obtained for each fastener 114 or group of fasteners 114 formed by their associated pusher member 130. By having the pressure sensors 126 staggered from the proximal to distal positions relative to the fasteners 114 within the surgical stapling apparatus 100, 200, the surgical stapling apparatus 100, 200 can be configured to determine deployment timing and completion of each fastener 114. This is valuable for controlling the surgical stapling apparatus 100, 200 with a controller 120 to verify limits with each specific cartridge 112 for clamping, distal stop, or home position. The controller 120 may have an analog or a microelectronic circuit.

As fastener 114 progression unfolds, the pressure responsive element 150 communicates a pressure signal 152 to the controller 120 through at least one communication means selected from the group comprising voltage, resistance, impedance, electromagnetism, radio frequency, current, inductance, capacitance, infrared, and optics. In operation, the pressure responsive element 150 tracks the applied pressure as the fasteners 114 are deployed and formed in progression (FIG. 5). In some cases, the applied pressure can be tracked in the form of waveform pulsations. When the controller 120 recognizes irregular pressure patterns represented by the pressure signal 152 communicated from the pressure responsive element 150, the controller 120 correspondingly registers an error and may be configured to emit an error code, emit a warning, stop fastener 114 formations, or even stop fastener 114 deployments.

The pressure responsive element 150 may also be configured for both linear and non-linear cartridge 112 configurations. It is envisioned that at least one of the jaws 108, 110, preferably the first jaw 108, includes a non-linear cartridge. In other words, the pressure responsive element 150 can be used for linear cartridge 112 surgical stapling apparatuses 100, 200 or non-linear cartridge 112 surgical stapling apparatuses 100, 200 including curved, circular, or any other geometrically-shaped cartridge 112 required to assess fastener quality or progression status.

Figure 11:
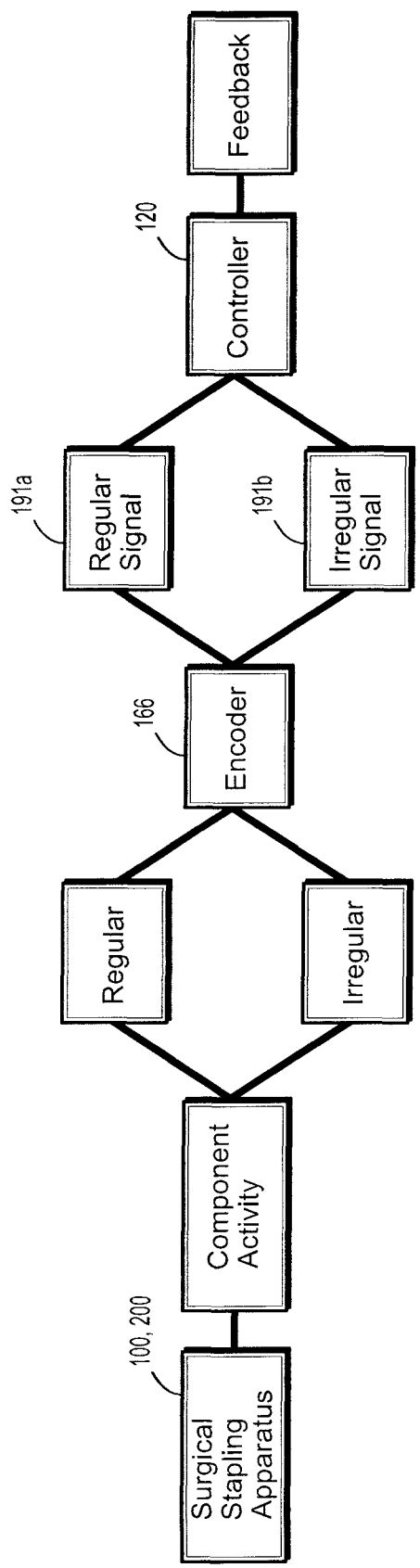
FIG. 11 is a schematic of the encoder feature according to one embodiment of the present disclosure.

Often, the surgical stapling apparatus 100, 200 can include a knife 164. In one manifestation of the present disclosure, the surgical stapling apparatus 100, 200 is configured and dimensioned such that the controller 120 prevents the knife 164 from cutting. In other words, the controller 120 includes an encoder 166, i.e., a knife cutting prevention feature. As seen in FIG. 11, one configuration contemplates the encoder 166 configured to recognize irregular behaviour of the surgical stapling apparatus 100, 200. In some instances, the encoder 166 is configured and dimensioned to recognize component positions relative to the pressure applied. The components of which are selected from the group comprising the actuation mechanism 138, knife 164, actuator 136, actuation sled 132, pusher member 130, first jaw 108, and second jaw 110, or any combination thereof. The encoder 166 can be rotational, or even linear.

Figure 9:
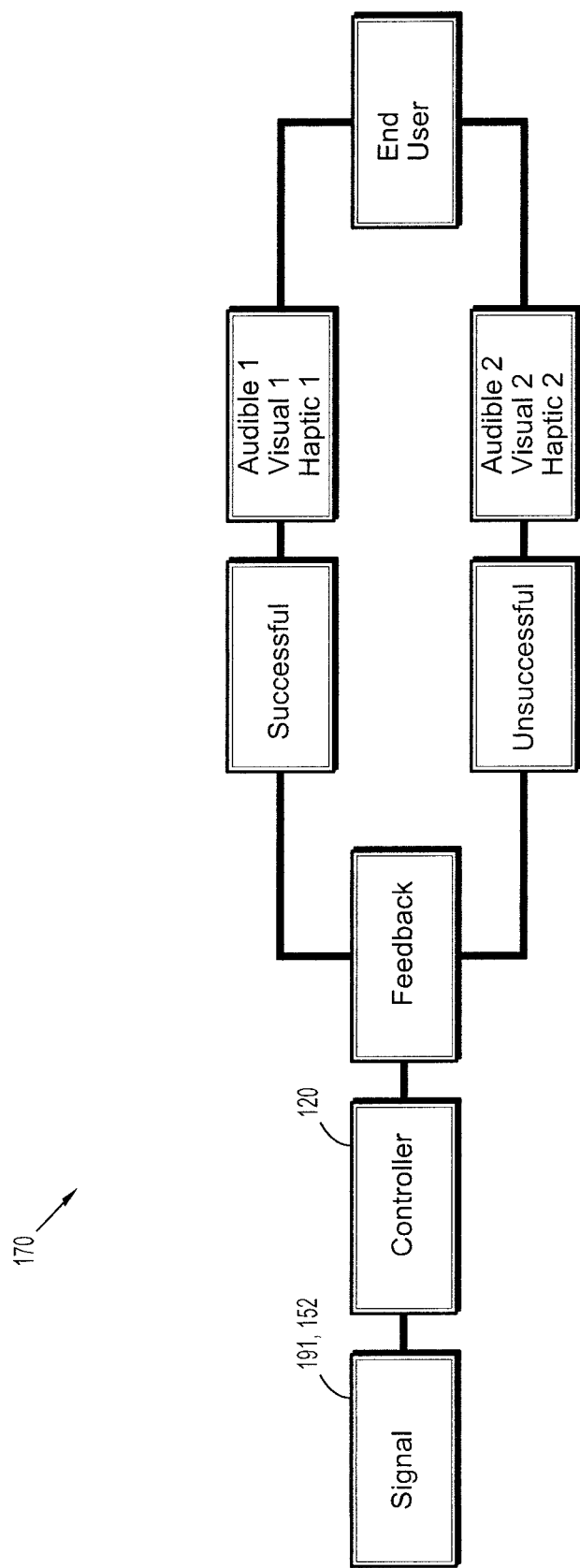
FIG. 9 is a schematic view of the end user feedback communication feature according to one embodiment of the present disclosure.

Referring to FIG. 9, the controller 120, in some manifestations, includes an end user feedback communication feature 170. The end user feedback communication feature 170 is configured to communicate feedback to an end user after receiving and deciphering a signal 152, 191 through at least one means selected from the group comprising audible (bells, speech, buzzers, beeps, etc.), visual (lights, LED's, LCD, or electroluminescent screens of varying colors, text, and/or symbols), and tactile (vibratory). For example, the feedback may be configured to indicate the successful or unsuccessful completion of a task such as initiation of fastener deployment progression, completion of fastener deployment and formation, individual fastener deployment, individual fastener formation, or other similar tasks recognized by a person of ordinary skill in the art.

To protect the circuit 124 from tearing or abrasion and to attain accurate, repeatable feedback, a thin, hard surface material such as Kapton® polyimide film or a foil of titanium or steel alloy or a flash coated nickel, chrome or nitride coating can be laminated onto the top layer of the circuit 124, defining a laminate 158. Furthermore, a lubricant coating 160 may also be applied to the laminate layer.

The lubricant coating 160 is any low friction plastic, grease, PTFE blended material, or any other comparable lubricant. The lubricant 160 is beneficial for achieving a quality output pressure signal 152 and for improving the robustness of working components.

Figure 10:
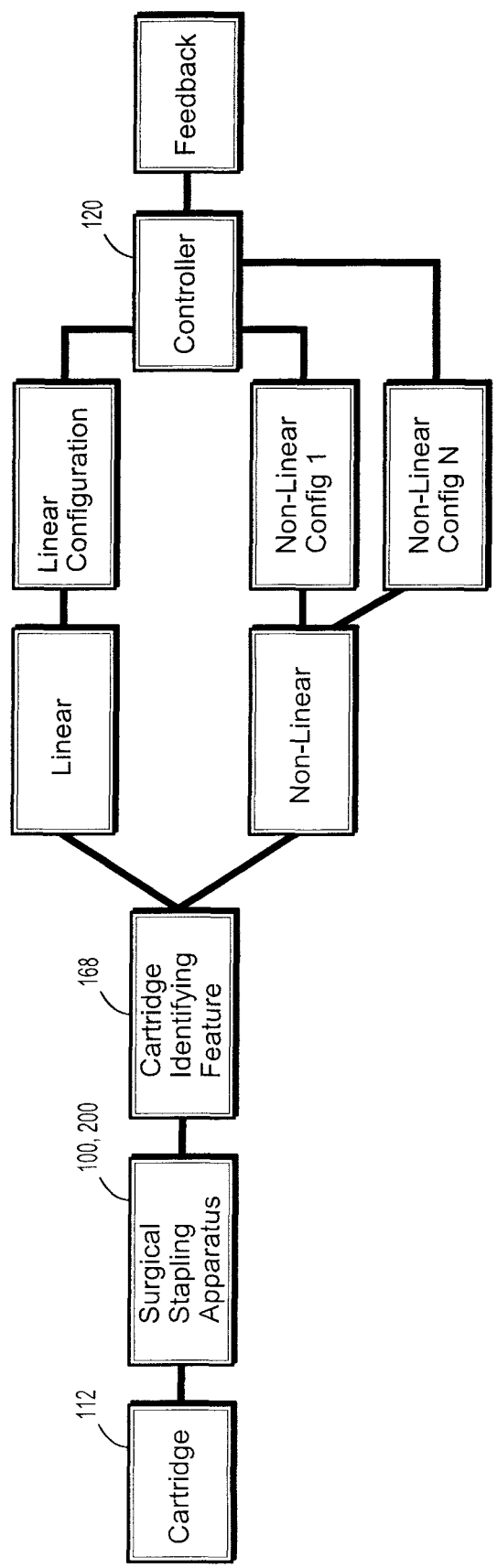
FIG. 10 is a schematic view of the cartridge identifying feature according to one embodiment of the present disclosure.

As seen in FIG. 10, the surgical stapling apparatus 100, 200 may have a circuit 124 including a cartridge identifying feature 168. In particular, the pressure responsive element 150 includes at least one circuit 124, wherein each circuit 124 has a specific electrical range or value of resistance, inductance, or impedance that can be read by the controller 120 to determine the exact type of cartridge 112 or end effector 106 loaded for identification. With this feature, the surgical stapling apparatus 100, 200 includes a controller 120 configured to set cartridge 112 or fastener 114 specific positional limitations and/or run mode.

Figure 4A:
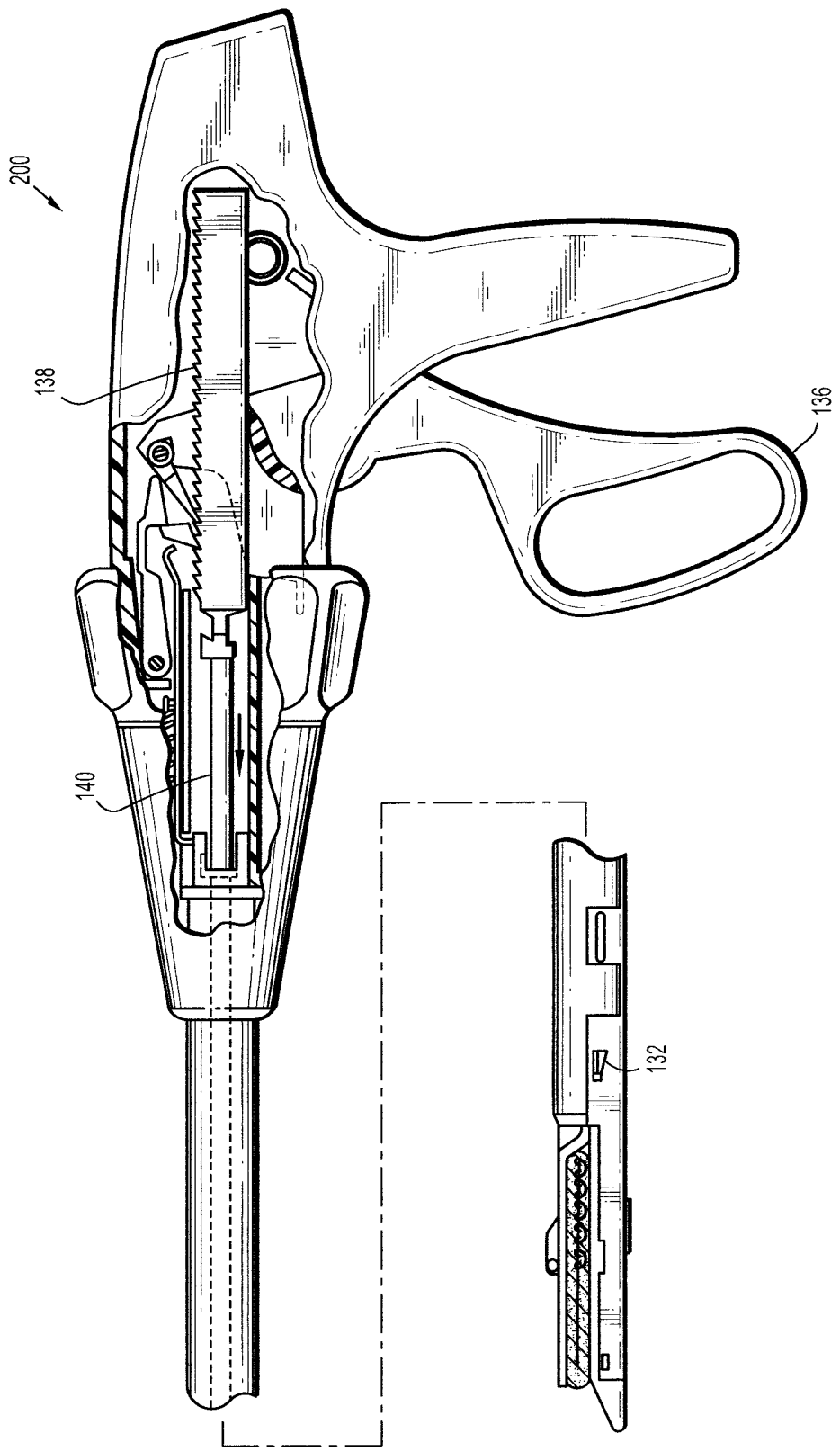
FIG. 4A is a side elevational view of the surgical stapling apparatus of FIG. 1B with the housing sectioned to illustrate the actuation mechanism when the actuator is manipulated through one an actuation stroke to apply a portion of the fasteners from the cartridge to tissue.
Figure 4B:
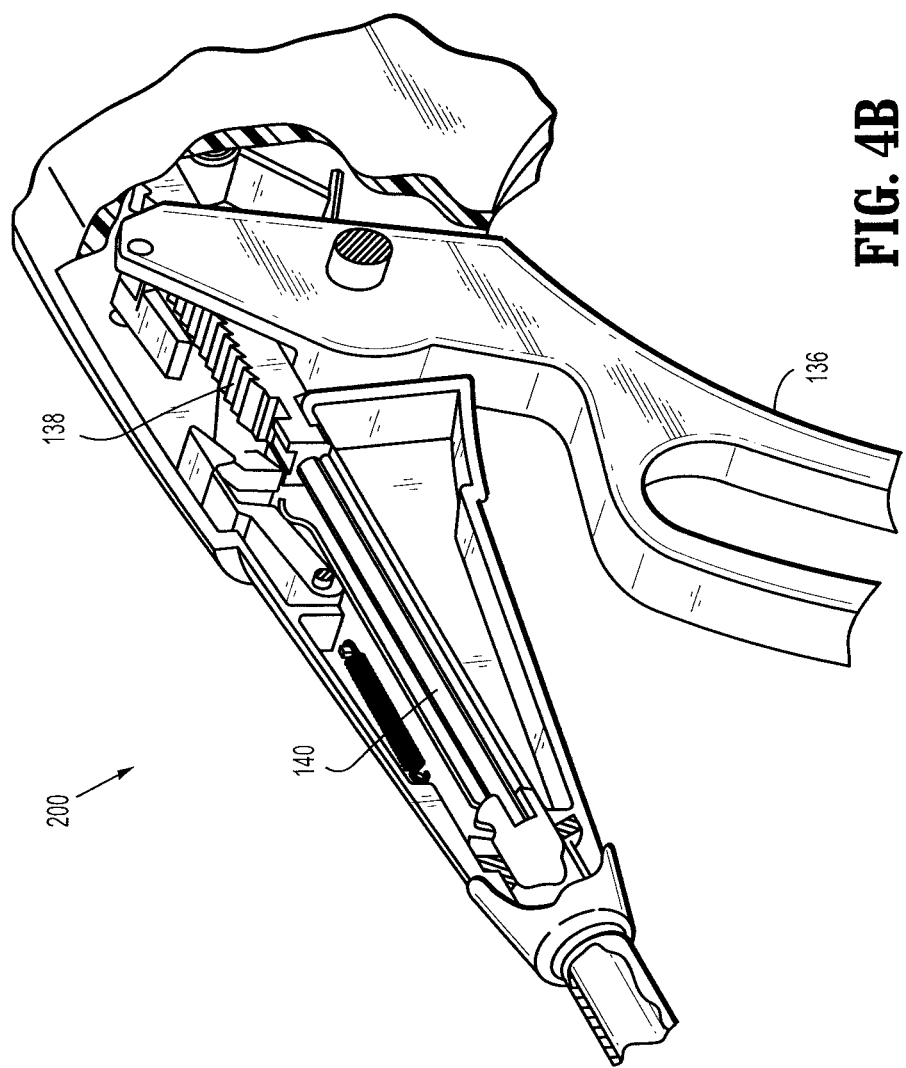
FIG. 4B is a perspective view in partial cross-section of the surgical stapling apparatus of FIG. 4A in accordance with the present disclosure.

In operation, when an end user (not shown) actuates the actuator 136, the actuating mechanism 138 causes the actuation sled 132 to interact with the pusher members 130 (FIG. 4A). In certain variations, the actuator 136 includes separate actuating features for actuating the actuation sled 132 and the first and second jaws 108, 110. For example, an actuation sled actuator 136a is used to remotely actuate the actuation sled 132, and a jaw actuator 136b is used to actuate first and second jaws 108, 110. Alternatively, a single actuator 136 is used to actuate both the actuation sled 132 and the jaws 108, 110. In another example, separate actuators 136 are connected to the individual first and second jaws 108, 110.

Figure 1D:
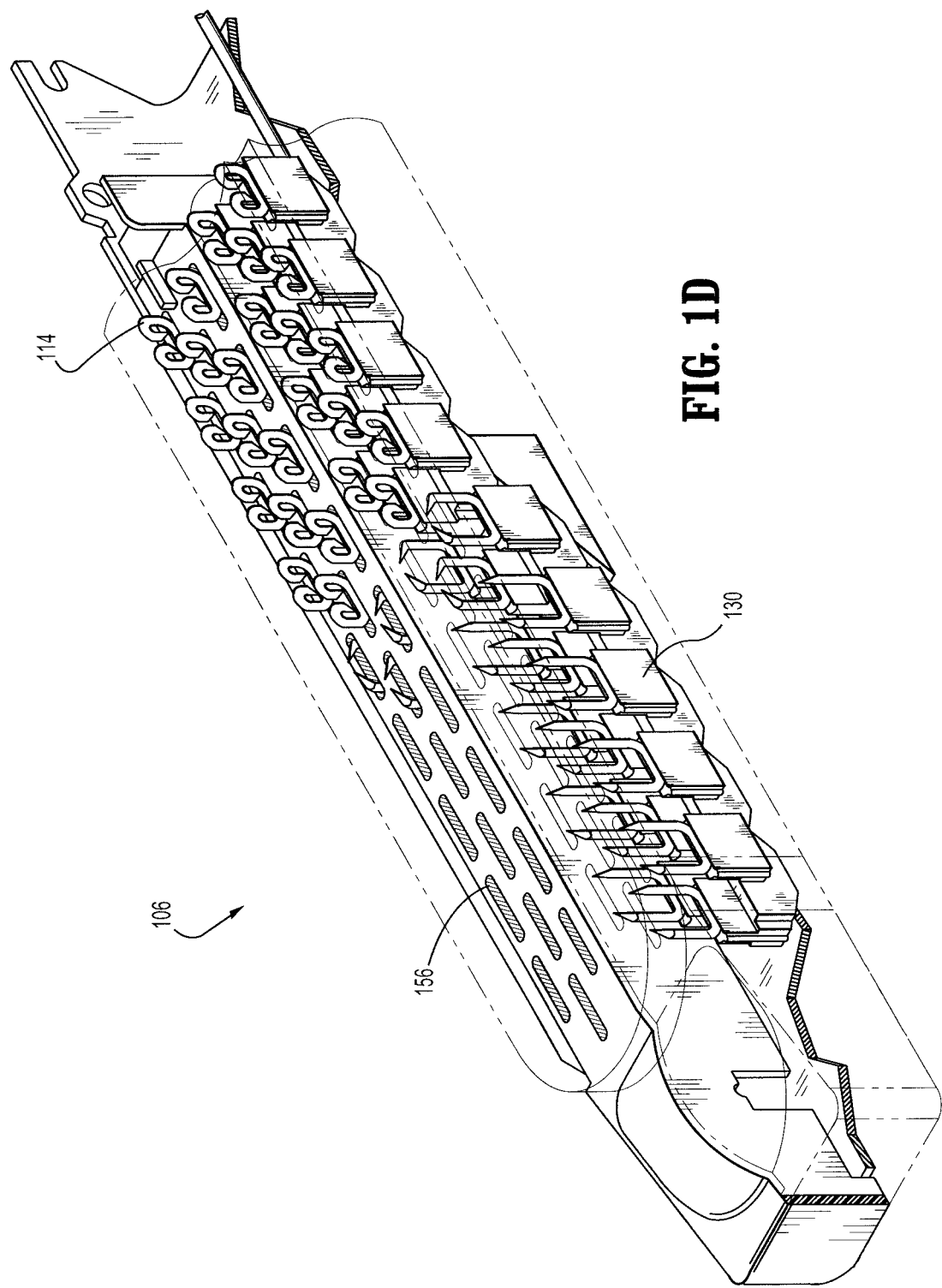
FIG. 1D is a perspective view of the end effector during a fastener applying operation as the wedge translates through the cartridge to sequentially eject the fasteners from the cartridge and drive them against one of the jaws to be formed thereby.

Upon actuation, the actuation sled 132 wedges the pusher members 130 upwards, forcing the fasteners 114 up into the opposing second jaw 110 surface, and in particular, into fastener-forming pockets 156 (FIG. 1D). From FIG. 1D, in its initial configuration the fastener 114 is shaped in a substantially U-shaped configuration. In its fully formed configuration, the faster 114 is shaped in a substantially B-shaped configuration. In the process of transforming the fastener 114 from the first configuration to the second configuration, the second jaw 110 acts as an anvil and correspondingly compresses the fastener 114 into its second configuration B-shape as the fastener prongs 114a, 114b engage the fastener-forming pockets 156. This resulting pressure applied to the pressure responsive element 150 is therefore a result of the interaction between the actuation sled 132 and the pusher members 130.

In embodiments where the pressure responsive element 150 includes a circuit 112 disposed within the cartridge channel 128, the downward force of the second jaw 110 onto the upwardly driving fastener 114, pusher member 130, and actuation sled 132 combination consequently causes reaction forces to pass through fasteners 114, pusher member 130, and actuation sled 132 combination in the opposing downward direction and onto the circuit 112 and any pressure sensors 126, which correspondingly register the applied pressure. The pressure responsive element 150 then communicates a pressure signal 152 to the controller 120, where the pressure signal 152 is representative of the pressure applied to the pressure responsive element 152. The controller 120 receives the pressure signal 152 and selectively emits a response or feedback based on the pressure signal 152.

In certain embodiments, the pressure responsive element 150 includes a circuit 112 disposed on the external surface of one of the jaws 108, 110. For example, when the circuit 112 is disposed on the external surface of the second jaw 110, applied pressure is displaced from the beam 162, which is connected to the actuation sled 132, onto the circuit 112 as both the beam 162 and the actuation sled 132 translate longitudinally along the first and second jaws 108, 110. In other words, as the actuation sled 132 translates and engages the pusher members 130, the pusher members 130 drive fasteners 114 up into the second jaw 110 and fastener-forming pockets 156. This consequently causes downward reaction forces to be displaced to the beam 162 onto the circuit 112 as the actuation sled 132 pulls down the beam 162 from the resultant downward reaction forces from the fastener-forming pockets 156 pass through the fasteners 114 and pusher members 130 onto the actuation sled 132. The pressure sensors 126 correspondingly register the applied pressure. The pressure responsive element 150 than communicates a pressure signal 152 to the controller 120, where the pressure signal 152 is representative of the pressure applied to the pressure responsive element 152. The controller 120 receives the pressure signal 152 and selectively emits a response or feedback based on the pressure signal 152.

In embodiments that include an encoder 166, the encoder 166 is configured to recognize the irregular behaviour of a component of the surgical stapling apparatus 100, 200 the components of which can be selected from the group comprising the actuation mechanism 138, knife 164, actuator 136, actuation sled 132, pusher member 130, first jaw 108, and second jaw 110. In one example where the encoder 166 is configured to monitor the positions of the knife 164, and where the encoder 166 recognizes an irregular position of the knife 164, the encoder 166 communicates the irregularity to the controller 120 via an encoder signal 191, the signal either regular 191a or irregular 191b. Upon receiving an irregular signal 191b, the controller 120 registers an error code, and in some instances, is configured to prevent cutting without fastening.

The encoder 166 communicates the encoder signal 191 to the controller 120 through at least one means selected from the group comprising voltage, resistance, impedance, electromagnetism, radio frequency, current, inductance, capacitance, infrared, and optics. It is also envisioned that the controller 120 is configured and dimensioned to receive an encoder signal 191 from the pressure responsive element 150 and to determine fastener 114 deployment and formation disparities with respect to the component behaviour, e.g., the knife's 164 irregular positioning. The controller 120 is also configured and dimensioned to initiate an error code or modify fastener 114 deployment settings.

Turning now to FIGS. 12-16, a surgical device or end effector, for a powered surgical stapling apparatus according to another embodiment of the present disclosure, is shown and generally designated 500. End effector 500 includes a parallel separating jaw system wherein opposing jaws remain parallel relative to each other during approximation and separation. End effector 500 is configured to be capable of connection to powered, rotating drive shafts of an electromechanical power source (not shown).

Figure 12:
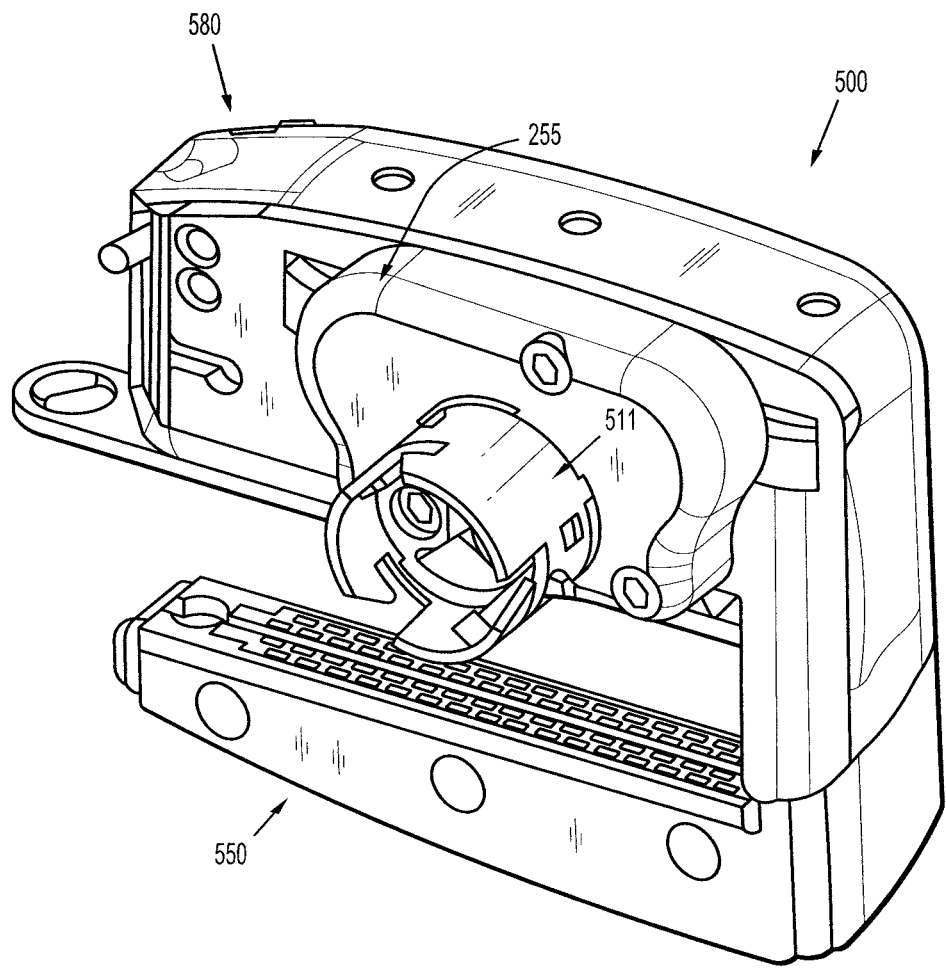
FIG. 12 is a perspective view of a surgical device or end effector for a powered surgical stapling apparatus according to another embodiment of the present disclosure.
Figure 13:
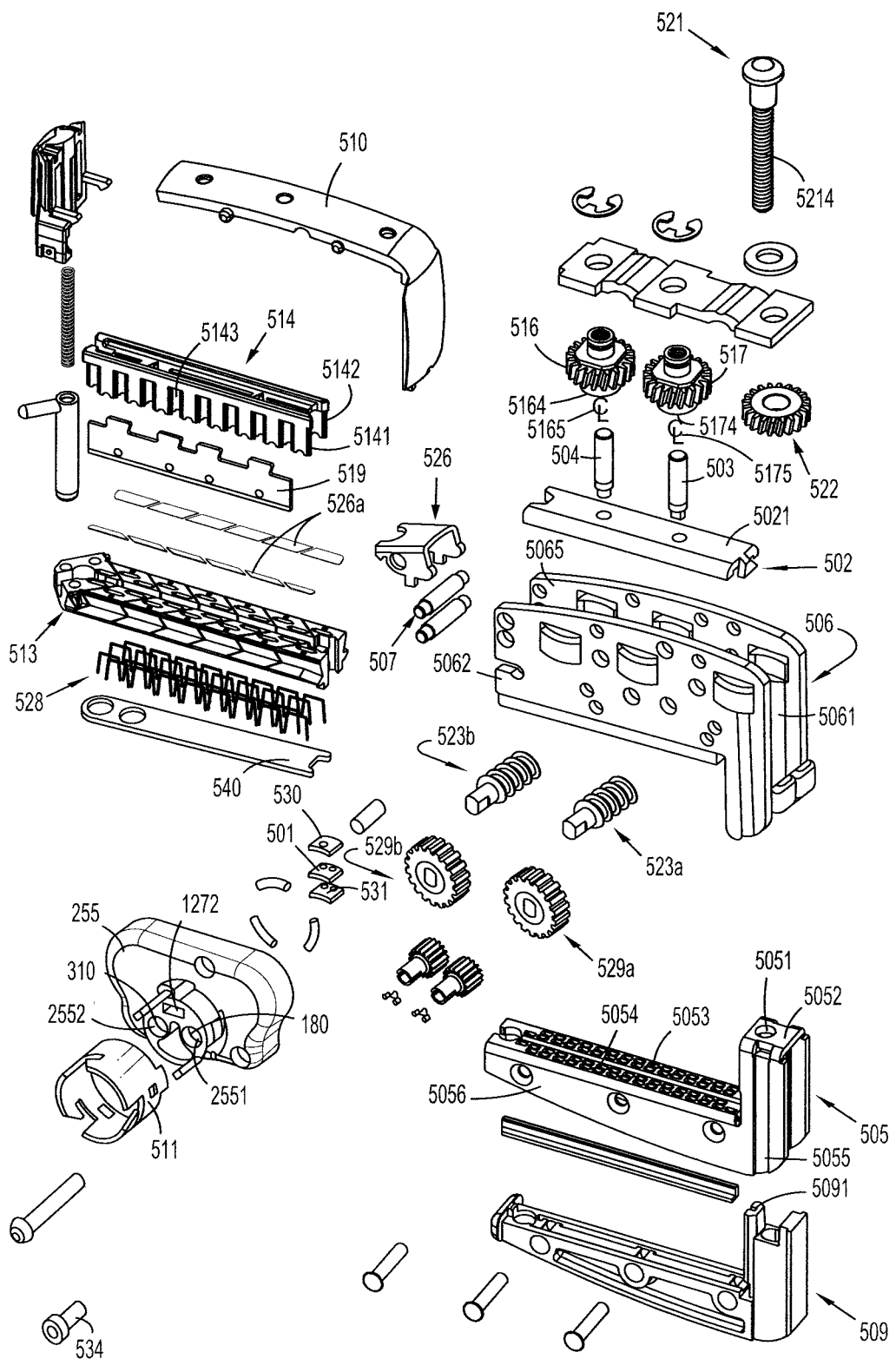
FIG. 13 is an exploded perspective view of the surgical device or end effector of FIG. 12.

As seen in FIGS. 12 and 13, end effector 500 includes a first jaw 580 and a second jaw 550, wherein the first jaw 580 and the second jaw 550 are in contact with each other at their respective first ends so as to enable parallel approximation and separation.

As seen in FIG. 13, the second jaw 550 includes an anvil 505 having a vertically-disposed, internally-threaded bore 5051 at its upper end 5052, and a plurality of staple guides 5053 arranged in parallel rows along a region 5054 of the anvil 505 that is opposite to, and corresponds to, the first jaw 580.

With continued reference to FIG. 13, first jaw 580 includes a housing frame 506 defining a pair of internally disposed guides 5061 along which a pair of ribs 5055 of the anvil 505 of second jaw 550 may travel, so that the housing frame 506 may move toward and away from the anvil 505 while remaining parallel with the anvil 505.

A gear housing 255 is mounted to one side 5062 of the housing frame 506. A quick-connect coupling 511 is mounted onto the gear housing 255. A memory module 501 is arranged in the gear housing 255 and includes a connector 2554 that extends through, or is accessible through, an opening 2553 of the gear housing 255. The memory module 501 is maintained in position within the gear housing 255 by an inboard shim 530 and an outboard shim 531. The gear housing 255 includes a first drive socket 180 and a second drive socket 310. In this embodiment, the first drive socket 180 of the gear housing 255 includes a first pinion 508a, and the second drive socket 310 of the gear housing 255 includes a second pinion 508b.

Each of the first and second pinions 508a and 508b engage respective first and second spur gears 529a and 529b. The first spur gear 529a non-rotatably engages a first worm 523a. The second spur gear 529b non-rotatably engages a second worm 523b. A threaded portion of each of the first worm 523a and the second worm 523b is disposed within the frame housing 506.

Also disposed within the frame housing 506 is a gear 522 which threadably engages the threaded portion of the first worm 523a. The gear 522 non-rotatably engages a screw 521. The screw includes externally-disposed threads 5214, which engage the internally-threaded bore 5051 of the anvil 505.

A first gear 516 and a second gear 517 are disposed within the frame housing 506. The first gear 516 and the second gear 517 are positioned on opposite sides of and engaged with the second worm 523b. Specifically, the first gear 516 engages a first side of the second worm 523b, and the second gear 517 engages a second side of the second worm 523b.

An externally-threaded screw 504 is disposed through an internally-threaded bore 5164 of the first gear 516, and an externally-threaded screw 503 is disposed through an internally-threaded bore 5174 of second gear 517. Since the first and second gears 516 and 517 are located on, and engage, opposite sides of the second worm 523b, the internally-threaded bores 5164 and 5174 of the first and second gears 516 and 517, as well as the externally-threaded screws 504 and 503, may be oppositely threaded relative to each other. Both screws 503 and 504 are fixedly coupled to a top surface 5021 of a thrust plate 502 that is positioned between opposite side walls of the housing frame 506.

A staple pusher 514 is attached to a bottom surface of the thrust plate 502. The staple pusher 514 includes parallel rows 5141 and 5142 of downwardly-disposed teeth 5143, each of which corresponds to and aligns with a staple guide 5053 of the anvil 505. A knife 519 having a cutting edge 5191 (shown facing downwardly in FIG. 13) is disposed between the parallel rows of downwardly-disposed teeth 5143 of the staple pusher 514.

A staple holder or cartridge 513 is disposed below the staple pusher 514. The staple cartridge 513 defines vertically-disposed slots 5132, each of which corresponds to and aligns with the downwardly-disposed teeth 5143 of the staple pusher 514 and with the staple guides 5053 of the anvil 505. A staple 528 is provided in each slot 5132. The staple cartridge 513 also includes a longitudinally-disposed slot 5131 through which knife 519 may be passed.

A staple retainer 540 is provided and is configured to cover the bottom surface of the staple cartridge 513 so as to maintain the staples 528 within the staple cartridge 513 and to prevent foreign material from entering the slots 5132 of the staple cartridge 513 during shipping of end effector 500.

A housing top 510 is provided and is arranged between the opposite sides 5062 and 5065 of the housing frame 506 and protects the components within the housing frame 506.

Reference may be made to U.S. patent application Ser. No. 10/094,051 (now U.S. Pat. No. 8,016,855), filed on Mar. 8, 2002, entitled "Surgical Device", the entire contents of which are incorporated herein by reference, for a more detailed discussion of the components, construction and operation of end effector 500. In addition, the end effector is connectable to a powered instrument handle which may include an elongate shaft. A separate, detachable shaft may also be used. As disclosed in U.S. Pat. No. 8,016,855, the shaft may be a flexible shaft extending from a housing and detachably attached thereto via a first coupling. The distal end of flexible shaft may include a second coupling adapted to detachably attach the end effector described above, to the distal end of the flexible shaft. The second coupling may also be adapted to detachably attach a different type of end effector. In another example embodiment, the distal end of the flexible shaft may be permanently attached to or be integral with a surgical instrument handle.

The shaft may include a first rotatable drive shaft and a second rotatable drive shaft, such as, for example, braided or helical drive cables. The drive shafts may be configured to transmit low torque but high speed, the high-speed/low-torque being converted to low-speed/high-torque by gearing arrangements disposed, for example, at the distal end and/or the proximal end of the drive flexible shaft, in the surgical instrument or attachment. Electro-mechanical driver elements disposed in a remote power console, or in a powered instrument handle, are used to operate the rotatable shafts.

In certain preferred embodiments, a controller is provided in the housing of a remote power console, or in the powered instrument handle, and is configured to monitor and/or control some or all functions and operations of the end effector attached to the flexible shaft, as well as the instrument as whole. A memory unit is provided and may include memory devices, such as, a ROM component, a RAM component, etc. The RAM and ROM components are in electrical and logical communication with controller via appropriate wiring. Memory units may also communicate with the controller, or other components, wirelessly.

Turning now to FIGS. 13-16, a more detailed discussion of end effector 500, including staple cartridge 513 according to the present disclosure, is provided. As seen in FIGS. 13-16, staple cartridge 513 is segmented along an axial length thereof. In particular, staple cartridge 513 is formed from a plurality of individual, separately movable body members or segments 513a extending axially along a length of staple cartridge 513. Each segment 513a is free to move in a direction transverse or orthogonal to a plane defined by the tissue contacting surface of staple cartridge 513.

Figure 14:
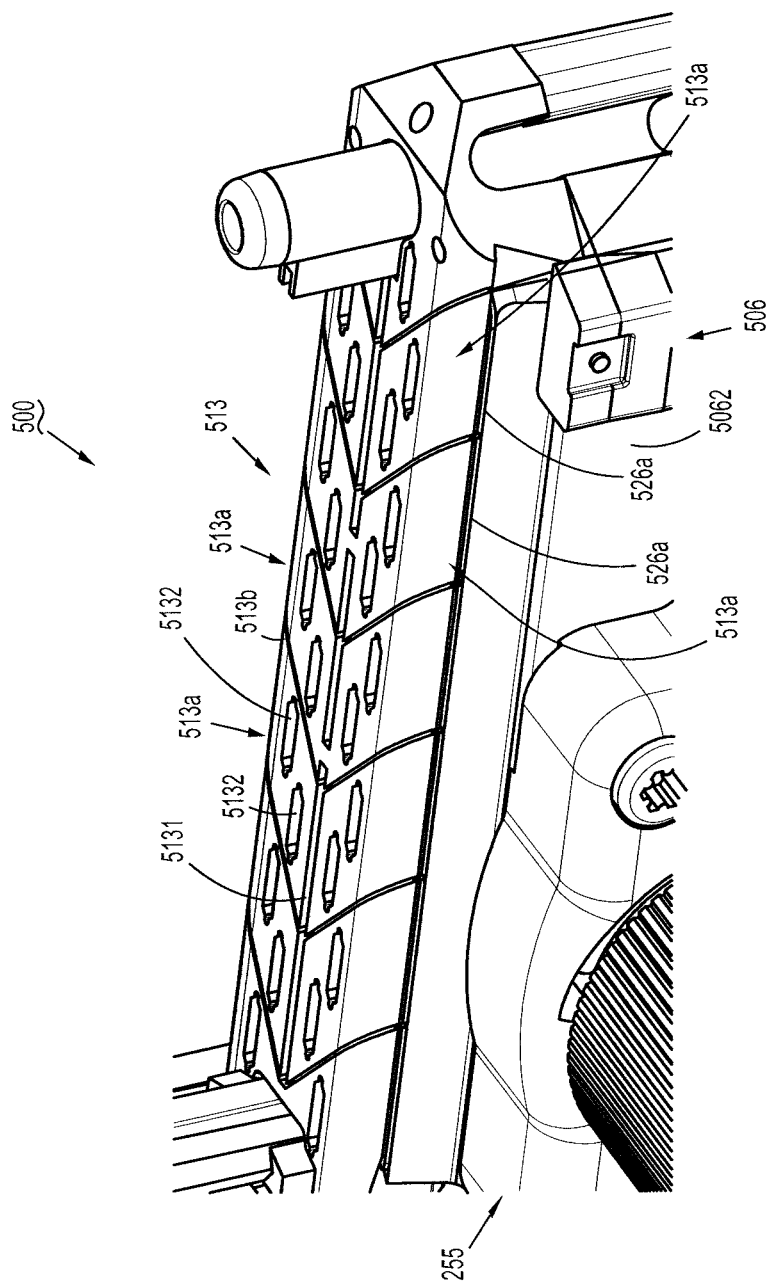
FIG. 14 is an enlarged perspective view illustrating a staple guide supported in a staple cartridge frame housing of the surgical device or end effector of FIG. 12.
Figure 15:
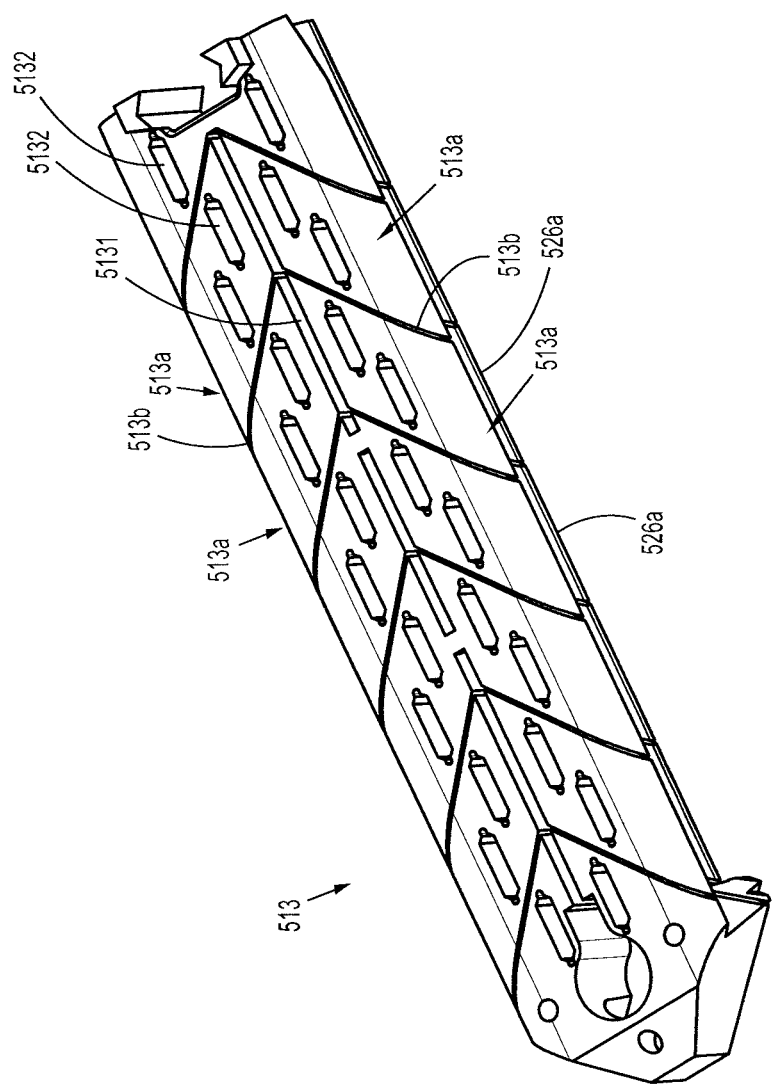
FIG. 15 is an enlarged perspective view of the staple guide of the surgical device or end effector of FIG. 12.
Figure 16:
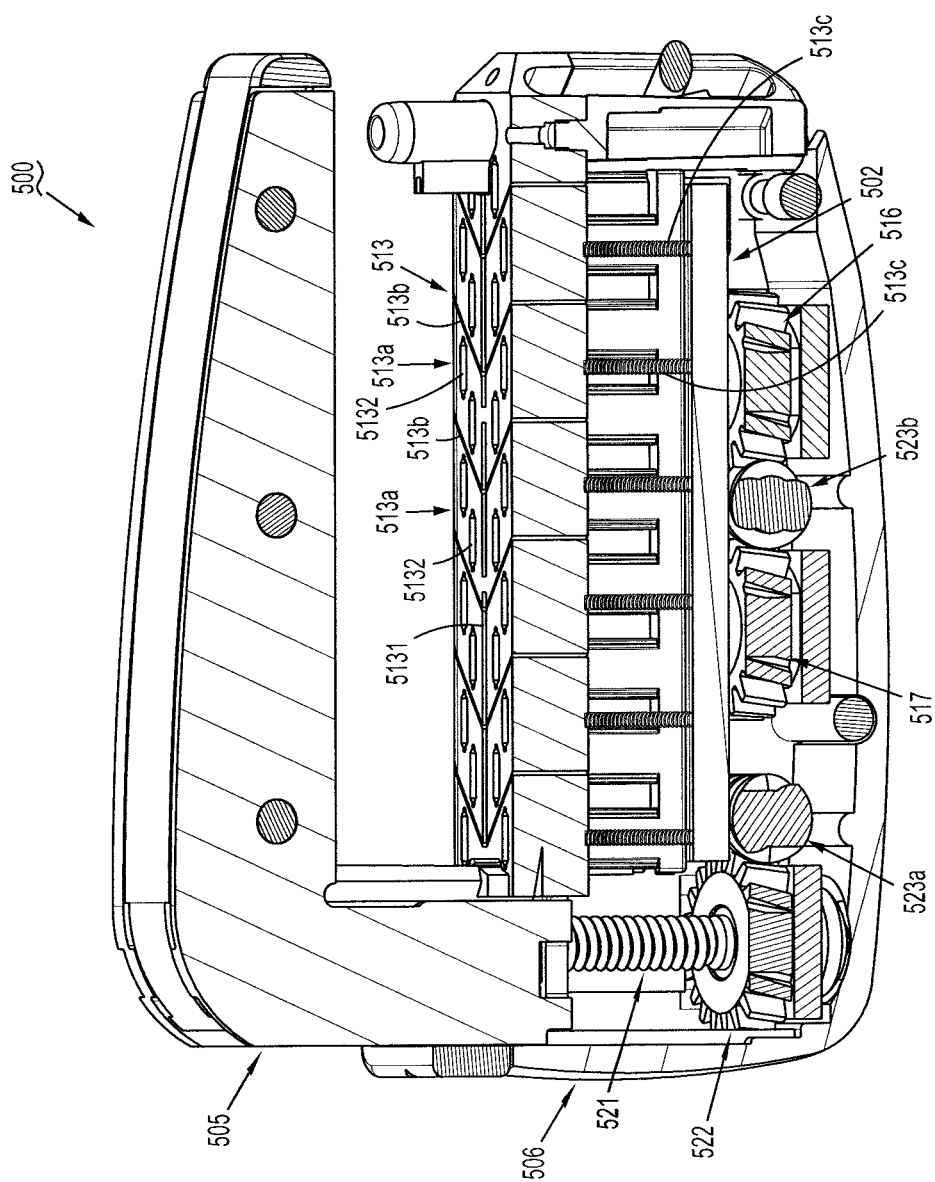
FIG. 16 is a cross-sectional view of the surgical device or end effector of FIG. 12, as taken through 16-16 of FIG. 12.

As seen in FIGS. 14-16, slots 5132, for retaining staples 528 therein, are arranged in at least two, longitudinally extending, parallel rows disposed on each side of knife slot 5131. The slots 5132 of each pair of rows are off-set or staggered with respect to one another, wherein the slots 5132 of one row are disposed between the slots 5132 of an adjacent row.

Each segment 513a of staple cartridge 513 is axially separated from one another by a transverse dividing line 513b that extends transversely across staple cartridge 513 and that does not extend across any staple slot 5132. In other words, the transverse dividing line 513b extends between axially adjacent slots 5132. Additionally, each segment 513a is sized so as to include a single slot 5132 from each of the adjacent rows of slots. However, it is contemplated that more than one slot 5132 from each row of slots may be disposed within each segment 513*a*.

With continued reference to FIGS. 14-16, end effector 500 further includes a pressure sensing film 526 interposed between staple cartridge 513 and sides 5062, 5065 of the housing frame 506. In particular, pressure sensing film 526 includes a plurality of individual pressure sensing film segments 526*a* interposed, one each, between respective segments 513*a* of staple cartridge 513 and sides 5062, 5065 of the housing frame 506.

As seen in FIG. 13, each segment 513*a* of staple cartridge 513 is floating above respective pressure sensing film segments 526*a* by respective biasing members 513*c*, in the form of compression springs. In particular, biasing members 513*c* are interposed between respective segments 513*a* of staple cartridge 513 and thrust plate 502 (see FIGS. 13 and 16) of end effector 500. In this manner, in use, the gap or distance from the tissue contacting surface of staple cartridge 513 to the tissue contacting surface of anvil 505 may adjust or vary depending on the thickness of tissue clamped between first jaw 580 and second jaw 550.

In accordance with the present disclosure, staple cartridge 513 of end effector 500, when coupled to an intelligent surgical device, instrument or apparatus 100, as described above, or when coupled to the electro-mechanical driver system, as shown and described in U.S. patent Ser. No. 10/094,051 (now U.S. Pat. No. 8,016,855), filed on Mar. 8, 2002, entitled "Surgical Device", the entire content of which is incorporated herein by reference, is capable of adjusting to accommodate different thicknesses present in a section of tissue that is clamped between first jaw 580 and second jaw 550.

Each pressure sensing film segment 526*a* is capable of sensing a force that is exerted on each segment 513*a* of staple cartridge 513 during a clamping or approximation of first jaw 580 and second jaw 550 and/or during a firing of end effector 500. Each segment 513*a* of staple cartridge 513 is spring loaded to a pre-set height, by biasing members 513*c*, during an unloaded or unclamped condition.

Each pressure sensing film segment 526*a* may be in electrical communication with the controller 120 (see FIG. 2). In this manner, signals sensed by pressure sensing film segments 526*a* may be transmitted to controller 120 for processing and/or analysis, and the processed and/or analyzed.

In operation, upon clamping or approximation (i.e., clamp up) of first jaw 580 and second jaw 550, each segment 513*a* of staple cartridge 513 becomes individually compressed (i.e., pressed against a respective pressure sensing film segment 526*a*) by the tissue by an amount dependent upon the force exerted on each section 513*a* of staple cartridge 513. Due to the floating nature of each segment 513*a* of staple cartridge 513, each segment 513*a* is capable of slight movement in a side-to-side or lateral direction and/or in a longitudinal direction.

The pressure sensing film segments, in certain embodiments, are connected to the controller and data are stored in the memory units and/or transmitted to other components. The memory units of the controller (which may be a remote unit, or may be incorporated in a powered instrument handle attached to the shaft and end effector) include data concerning desired parameters or ranges for the operation of the end effector and instrument as a whole. For example, the forces exerted on each segment 513*a* of staple cartridge 513 is determined by the pressure sensing film segments 526*a* in a manner substantially similar to pressure responsive element 150, as described above. The forces determined, detected of measured by pressure sensing film segments 526*a* may be displayed on a monitor, a display provided on the surgical device, or the like (not shown). It is contemplated that the monitor will display the forces exerted on each individual segment 513*a* of staple cartridge 513 as well as the overall force exerted on the entire length of the staple cartridge 513.

The forces measured by the pressure sensing film segments can be monitored over time. In other words, how the forces vary as the staples are ejected and formed against the anvil can be monitored, transmitted to the controller, transmitted to other components, stored in the memory units of the controller, compared to data concerning desired profiles for staple forming and/or used to provide information to the surgeon or used to affect the operation of the instrument.

Pressure sensors that can be used include but are not limited to electrical circuits that measure or monitor differences in one or more of resistance, conductance, impedance and capacitance. The sensor may incorporate one or more laminated layers of resistive and conductive substrates. Other sensors are contemplated.

In accordance with the present disclosure, the intelligent surgical device, instrument or apparatus 100, as described above, or the electro-mechanical driver system, as shown and described in U.S. patent application Ser. No. 10/094,051 (U.S. Patent Publication No. 2003/0130677), will be able to interpret a magnitude of the forces and determine whether conditions are acceptable to continue clamping/approximating first jaw 580 and second jaw 550 or if conditions are acceptable for firing of the end effector 500.

Additionally, in accordance with the present disclosure, the intelligent surgical device, instrument or apparatus 100, as described above, or the electro-mechanical driver system, as shown and described in U.S. patent application Ser. No. 10/094,051 (U.S. Patent Publication No. 2003/0130677), will be able to determine if obstructions are present in the tissue that is clamped between first jaw 580 and second jaw 550 and whether conditions are acceptable for firing of end effector 500 based on the loads and/or forces exerted on staple cartridge 513.

Accordingly, in view of the floating or spring biased nature of staple cartridge 513, and the segments 513*a* thereof, an adjustment or accommodation of staple cartridge 513 is more forgiving in tissues with inconsistent thicknesses, with obstructions and/or which are diseased. Additionally, the force sensing capability of staple cartridge 513 can provide the surgeon with an indication of the amount of compressive force each portion or segment of the tissue is under during a clamping/approximating of the first jaw 580 and second jaw 550 and/or during a firing of end effector 500. Also, since staple cartridge 513 is segmented and there are a plurality of pressure sensing film segments 526*a* disposed along an entire length of staple cartridge 513, the surgeon can be provided with information regarding the presence of an obstruction in the tissue clamped between first jaw 580 and second jaw 550 and an indication of the location of the obstruction along the length of staple cartridge 513.

By providing the surgeon with an indication of the location of the obstruction along the length of staple cartridge 513, the surgeon may move end effector 500 to another location or section of tissue, if necessary, in order to avoid hitting the obstruction during the stapling or firing procedure.

In operation, if the forces exerted on a particular segment 513*a* of staple cartridge 513 exceed a predetermined threshold value and/or if an average force exerted on staple cartridge 513 exceeds a predetermined threshold value, then the controller may register an error and may be configured to emit an error code, emit a warning and/or stop the firing procedure.

While several illustrative embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of preferred embodiments. Thus the scope of the embodiments should be determined by the appended claims and their legal equivalents, rather than by the examples given.

What is claimed is:

1. An intelligent surgical stapling apparatus, comprising:
a first jaw member and a second jaw member, the first jaw member having a first arm extending transversely from a proximal portion thereof, and the second jaw member having a second arm extending transversely from a proximal portion thereof, the first and second arms coupled together to enable movement between the first and the second jaw members;
a staple cartridge comprising:
opposed outer side surfaces;
a tissue contacting surface transverse to the opposed outer side surfaces and defining a longitudinal axis that extends between proximal and distal end portions of the tissue contacting surface, the tissue contacting surface defining a tissue contacting plane and positioned to extend distally along the longitudinal axis from the arms of the surgical stapling apparatus when the staple cartridge is coupled to one of the jaw members, the tissue contacting surface including a first segment and at least a second segment, each segment being movable relative to the other segment prior to a firing of the surgical stapling apparatus, each segment defining at least two staple receiving slots, each segment extending between an inner end portion and an outer end portion, the outer end portion of at least one of the segments extending to at least one of the opposed outer side surfaces of the staple cartridge, wherein the first segment is positioned on a support member, the first segment movable from a first position aligned with the tissue contacting plane to a second position away from the tissue contacting plane and closer to the support member;
an instrument handle; and
a controller in the instrument handle.

2. The surgical stapling apparatus according to claim 1, wherein the support member is a spring, and wherein the first segment is floating on the spring and is positioned to move towards the spring and away from the tissue contacting plane as the first segment moves from the first position to the second position.

3. The surgical stapling apparatus according to claim 2, wherein the first position is an expanded position and the second position is a depressed position relative to the second segment, wherein the spring is configured to urge the first segment toward the first position.

4. The surgical stapling apparatus according to claim 1, further comprising a sensor operatively coupled to at least one of the first and second segments.

5. The surgical stapling apparatus according to claim 4, wherein the sensor is a pressure sensor configured to sense a pressure from a movement of the at least one of the first and second segments.

6. The surgical stapling apparatus according to claim 4, wherein the sensor is disposed in electrical communication with the controller and a power source.

7. The surgical stapling apparatus according to claim 1, wherein the at least two staple receiving slots are arranged in longitudinally extending parallel rows.

8. The surgical stapling apparatus according to claim 7, wherein the at least two staple receiving slots are staggered longitudinally with respect to one another.

9. The surgical stapling apparatus according to claim 1, wherein the tissue contacting surface defines a knife slot that extends along the longitudinal axis between the proximal and distal end portions thereof, the knife slot separating the tissue contacting surface into a first side and a second side, the first segment being disposed on the first side of the knife slot, the second segment being disposed on the second side of the knife slot.

10. The surgical stapling apparatus according to claim 1, wherein at least one of the first and second segments is V-shaped and extends towards the longitudinal axis.

11. The surgical stapling apparatus according to claim 1, wherein at least one of the first and second segments is movable in at least one of a side-to-side direction and a longitudinal direction relative to the longitudinal axis, the side-to-side direction being transverse to the longitudinal direction.

12. The surgical stapling apparatus according to claim 1, further comprising a detachable shaft attached to the handle and the first and second jaw member.

* * * * *